US008851678B2

(12) United States Patent
Pelah et al.

(10) Patent No.: US 8,851,678 B2
(45) Date of Patent: Oct. 7, 2014

(54) VISUAL PERIMETER MEASUREMENT SYSTEM AND METHOD

(76) Inventors: Adar Pelah, York (GB); Louise Elizabeth Allen, Cambridge (GB); Michael Edward Slater, York (GB); Andrew Robert Jackson, York (GB)

(*) Notice: Subject to any disclaimer, the term of this patent is extended or adjusted under 35 U.S.C. 154(b) by 198 days.

(21) Appl. No.: 13/261,195

(22) PCT Filed: Aug. 24, 2010

(86) PCT No.: PCT/GB2010/001599
§ 371 (c)(1),
(2), (4) Date: Feb. 28, 2012

(87) PCT Pub. No.: WO2011/023948
PCT Pub. Date: Mar. 3, 2011

(65) Prior Publication Data
US 2012/0154751 A1    Jun. 21, 2012

(30) Foreign Application Priority Data
Aug. 28, 2009  (GB) .................................. 0915136.6

(51) Int. Cl.
A61B 3/02    (2006.01)
A61B 3/113   (2006.01)
A61B 3/00    (2006.01)
A61B 3/024   (2006.01)
A61B 3/14    (2006.01)

(52) U.S. Cl.
CPC .................. *A61B 3/024* (2013.01); *A61B 3/113* (2013.01); *A61B 3/0041* (2013.01); *A61B 3/14* (2013.01)
USPC ......................................................... 351/224

(58) Field of Classification Search
CPC ........................................................ A61B 3/024
USPC ................................................. 351/222–244
See application file for complete search history.

(56) References Cited

U.S. PATENT DOCUMENTS 3,664,732 A    5/1972  Lynn
3,737,217 A    6/1973  Haines et al.
(Continued)

FOREIGN PATENT DOCUMENTS

JP    2000-262472    9/2000
JP    2006-061461    3/2006
(Continued)

OTHER PUBLICATIONS

Johnston et al., "Computerised visual field test for children using multiple moving fixation targets", Medical & Biological Engineering & Computing, pp. 612-616, Nov. 1989.
(Continued)

Primary Examiner — Ricky Mack
Assistant Examiner — Robert E Tallman
(74) Attorney, Agent, or Firm — John Bruckner PC

(57) ABSTRACT

In one example of the invention a patient display is provided on which a fixation graphic or video is shown in substantially the center of the display, and then target graphics or video are shown at different positions on the display about the center. A test subject is positioned in front of the patient display a known distance therefrom, and a camera captures an image of the test subject's eyes, to allow gaze direction determination to be performed. The captured images are displayed to a clinician user by a controlling test application, the clinician making a determination based on the images as to whether the test subject saw a target graphic or video when it was displayed. The clinician user then makes an appropriate input into the controlling test application, which also logs the position at which the target image was displayed. By displaying target graphics at multiple locations on the screen and logging the clinician inputs, the controlling test application is able to build up a plot of the peripheral vision field of the test subject. This plot can then be graphically displayed to the clinician user, and stored with the test results for future clinical use.

3 Claims, 16 Drawing Sheets

(56) References Cited

U.S. PATENT DOCUMENTS

| | | | |
|---|---|---|---|
| 3,883,235 A | | 5/1975 | Lynn et al. |
| 3,984,156 A | | 10/1976 | Jernigan |
| 4,675,736 A | * | 6/1987 | Lehmer et al. ............... 348/747 |
| 5,801,810 A | | 9/1998 | Roenker |
| 2004/0057013 A1 | | 3/2004 | Cappo et al. |
| 2010/0149488 A1 | * | 6/2010 | Lo et al. ...................... 351/206 |

FOREIGN PATENT DOCUMENTS

| | | |
|---|---|---|
| WO | WO 99/22638 | 5/1999 |
| WO | WO 00/57772 | 10/2000 |
| WO | WO 2004/093668 | 11/2004 |
| WO | WO 2008/106802 | 9/2008 |
| WO | WO 2008/139137 | 11/2008 |

OTHER PUBLICATIONS

Accornero et al., "Computerized video screen perimetry", Arch. Ophthalmol—vol. 102, p. 40-41, Jan. 1984.

Suga et al., "Development of a quantitative perimeter screening system for young children based on an immersive VR display", Electronics and Communications in Japan, Part 2, vol. 89, No. 11, pp. 31-39, 2006.

The international search report and the written opinion of the international searching authority from PCT/GB2010/001599, date of mailing Feb. 3, 2011.

Search Report from GB0915136.6, dated Dec. 21, 2009.

Search Report from GB0915136.6, dated Apr. 30, 2010.

Search Report from GB0915136.6, dated May 11, 2010.

Communication Dispatch No. 241064 from counterpart foreign Japanese application 2012-526113 (mailing date of Dispatch: May 7, 2014).

"DS Soft All Catalogue 08 Summer", Mainichi Communications Inc., Aug. 1, 2008, vol. 13, No. 8, pp. 256-257.

Shunya Matsumoto, "Visualized process for the visual field test", Japan, Kanehara Co., Ltd., Apr. 20, 2007, Second edition the first print, pp. 68-71.

* cited by examiner

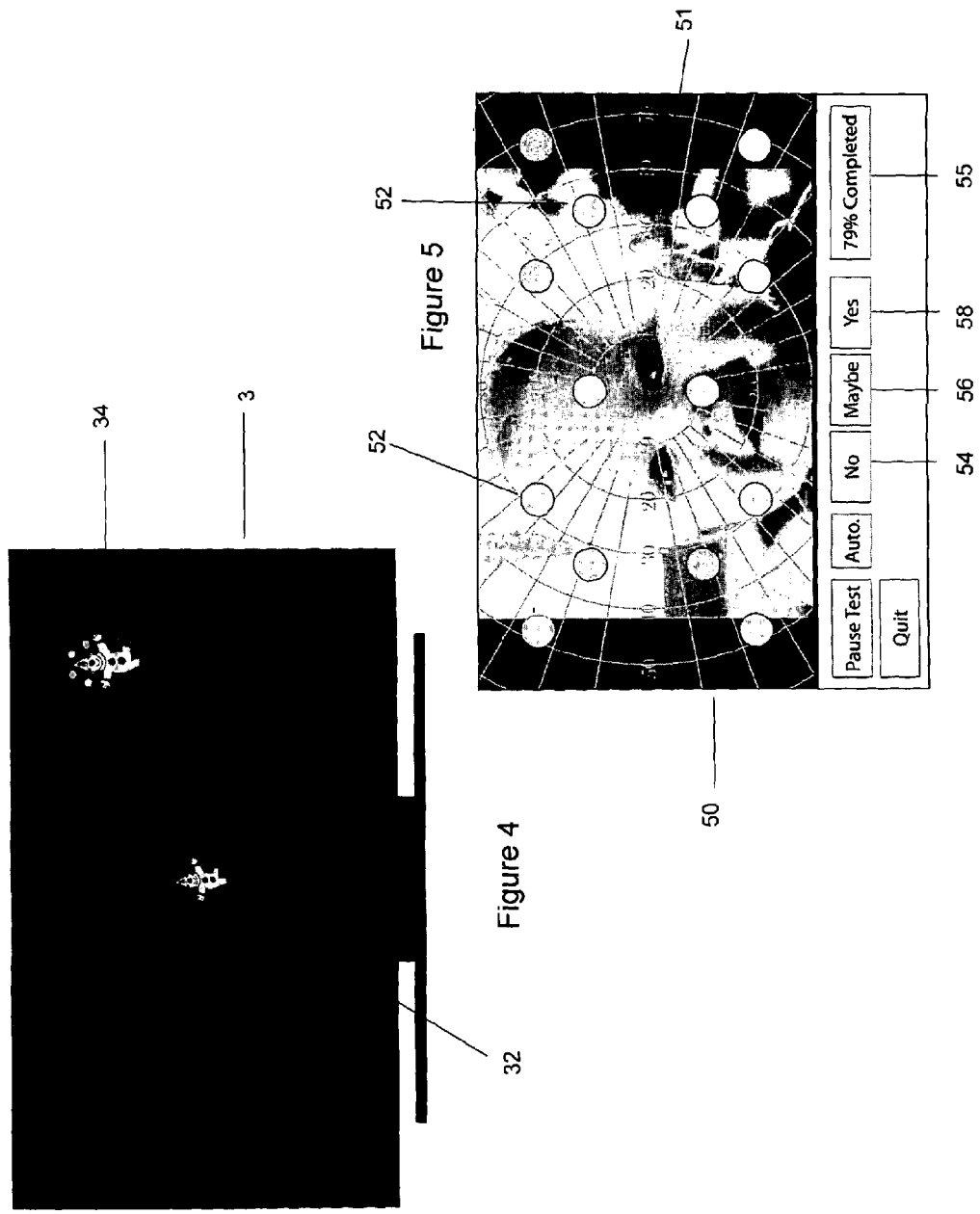

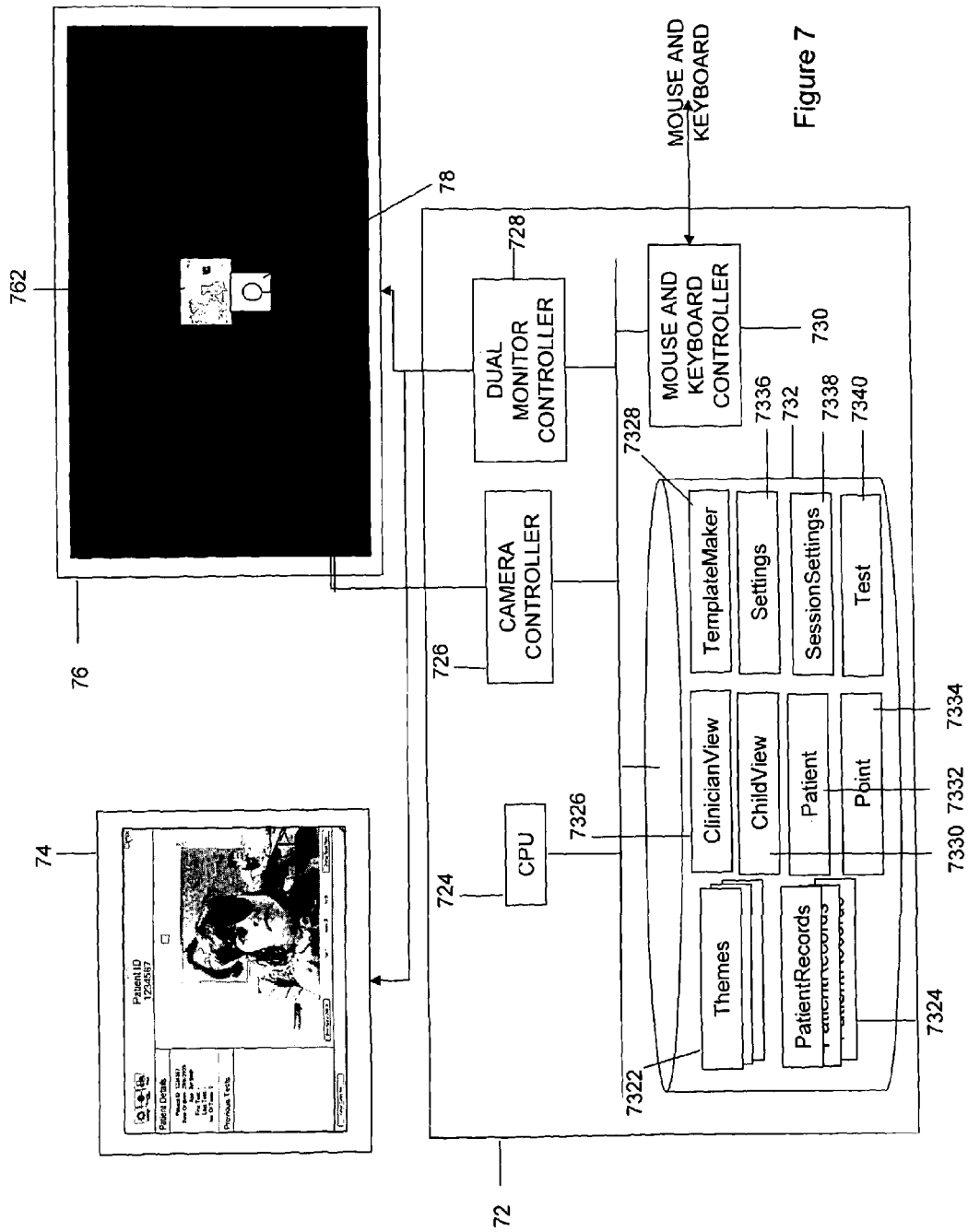

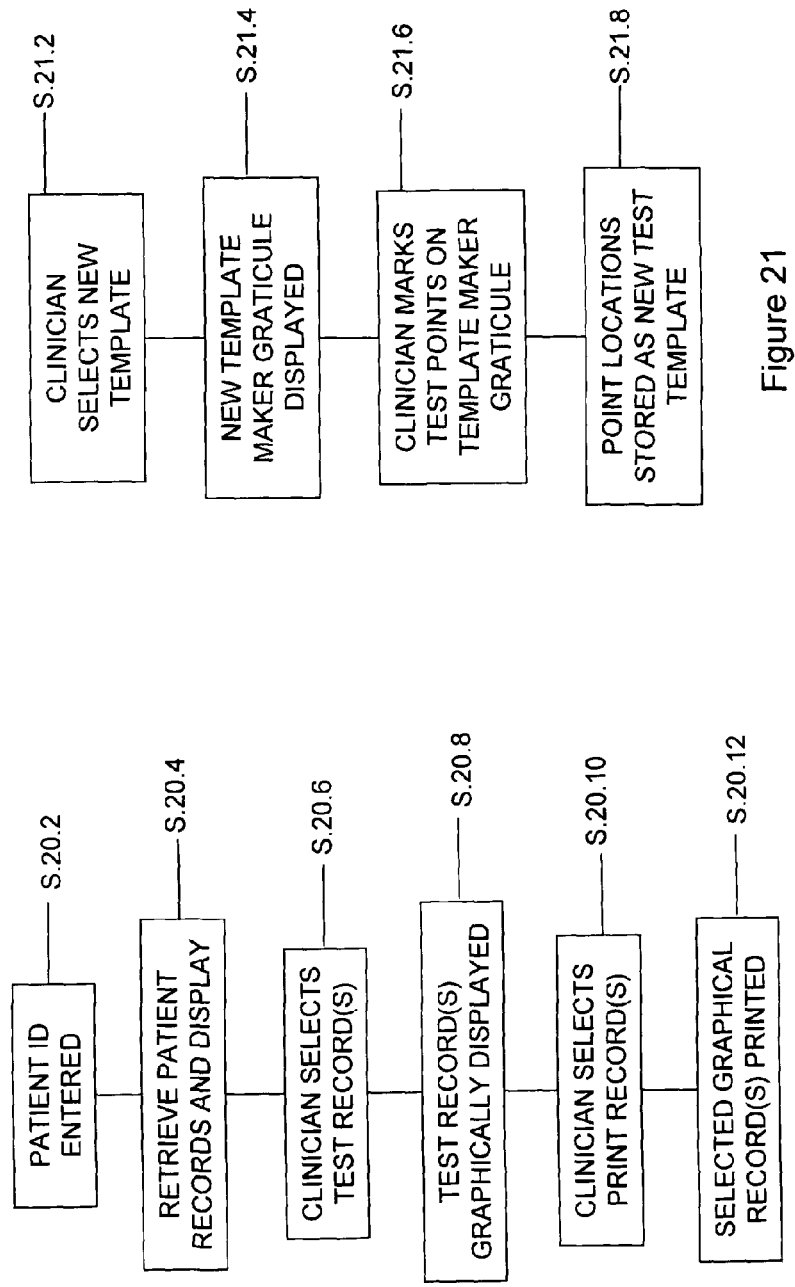

VISUAL PERIMETER MEASUREMENT SYSTEM AND METHOD

TECHNICAL FIELD

Examples of the present invention relate to a visual perimeter measurement system and method.

BACKGROUND TO EXAMPLES OF THE INVENTION

Accurate measurement of peripheral vision in a human can lead to early diagnosis of potentially serious medical conditions. Causes of visual field deficit include neonatal brain haemorrhage or stroke and eye conditions such as retinitis pigmentosa and glaucoma, additionally over 50% of childhood brain tumours present with visual impairment.

A human eye converts light entering it into neural signals which are then sent down the optic nerve. Thus, the left optic nerve carries all of the visual information from the left eye, and the right optic nerve carries all of the visual information from the right eye. The optic nerves meet at the optic chiasm within the brain. Within the optic chiasm nerve fibres carrying visual information from the visual field temporal (lateral) to the vertical mid-line, cross to the other side. The resultant right optic tract therefore consists of nerve fibres subserving the temporal visual field of the left eye and the nasal visual field of the right eye and the left optic tract consists of nerve fibres subserving the temporal visual field of the right eye and the nasal visual field of the left eye these are called homonymous visual hemi-fields. The optic tracts carry the left and right homonymous hemi-field information to the occipital lobe of the brain. The left homonymous visual hemi-field is processed by the right occipital cortex and the right homonymous visual hemi-field is processed by the left occipital cortex.

The pattern of visual field loss will therefore allow the clinician to determine the position of a tumour or brain injury. An ocular abnormality such as glaucoma or retinal detachment will cause a visual field defect which crosses over the vertical mid-line. A tumour on or touching the optic nerve will result in loss of the central visual field in one eye along with reduction of central visual acuity. Tumours involving the optic chiasm often do not initially affect central visual acuity but interrupt the nerve fibres subserving the temporal visual field as they cross within the chiasm—causing a temporal hemi-field loss in both eyes (bitemporal hemianopia). Bitemporal hemianopias do not usually cause symptoms of visual disturbance but are important to detect in order to diagnosis a chiasmal tumour at an early stage. Tumours or brain injury involving the optic tract and occipital cortex will cause a homonymous visual field defect—for example a tumour in the right occipital lobe will cause loss of the temporal hemi-visual field from the left eye and the nasal visual field in the right eye. This would be termed a left homonymous hemianopia.

Accurate measurement of peripheral vision can be a first indicator of brain tumours and, as described, the pattern of visual field loss can localise the tumour or other pathology. Serial measurements of the peripheral visual field defect can aid in the monitoring of tumour growth and indicate if further therapy is required.

Several techniques are known for measuring peripheral vision of a human patient. Two common perimetry measurement apparatuses are the "Goldman perimeter", and the "Humphrey field analyser". However, both sets of apparatus require the human patient to place their head into an enclosed compartment, and to maintain their vision at a fixation point in the centre of the compartment, suppressing their reflexive eye movement toward the appearing target in the visual periphery. Such techniques are therefore difficult to use with small children, for example, because small children find the test extremely intimidating, and are unable to maintain visual fixation at the central point in accordance with the test instructions appropriately. Similarly, elderly patients who may be suffering from degenerative brain diseases also present the same problems.

In order to get around such problems various other techniques have been developed to try and measure peripheral vision in small children. FIG. 1 illustrates a diagram from Suga et al, "Development of a Quantative Perimeter Screening System for Young Children Based on an Immersive VR Display", Electronics and Communications in Japan, Part II, Volume 89, No. 11, 2006. Here, a virtual reality technique is used to construct a pseudo video space. The immersive display device has three screens measuring 3 m×2.25 m on the front and the two sides, and also a 3 m×1 m vertical screen at the bottom. The system includes four projectors to produce video images on the respective screens, four computers to send the video signals to the projectors, and a computer to provide synchronisation signals to these computers.

In order to provide a fixation point for the child subject, a video image which attracts the attention of the subject is used. Then, while the video image is being displayed at the fixation point, image targets, which are simply round circles of light, are made to appear on peripheral screens. A single camera is provided focused on the subject's face, and image processing is used to determine the view line of the subject i.e. the direction of gaze of the subject, using template matching. At the time a target is displayed, if, as a result of the image processing it is determined that the subject view line changes within one second of the target presentation in a direction agreeing with the direction of the target presentation, it is judged that the target has been recognised.

The Suga et al system therefore presents an attempt at producing an automated perimeter measurement system, using image processing of the subject to try and determine the subject's direction of gaze, and whether a target has been detected. However, the system is extremely complicated, requiring much space, and equipment to set up. In addition, the actual criterion by which it is judged whether a target has in fact been seen is open to error, as a decision is made purely based on whether the subject looks towards the direction of the target, but not whether in fact the target has been seen.

Other, manual, techniques are also known. FIG. 2 illustrates the "white sphere kinetic arc" method. Using a white ball as a fixation point, another white ball is moved into a child's visual field by a clinician, and the child's response is monitored by a second clinician. This method requires two clinicians, and the movement of the second clinician may be distracting, leading to an inaccurate test. As such, this method is far from ideal, delivering a potentially poor result, as well as being costly to administer.

There is thus a need for a visual perimeter measurement system that can be used with small children, and that will provide more reliable, accurate, and consistent results.

SUMMARY OF EXAMPLES OF THE INVENTION

In one example of the invention a patient display is provided on which a fixation graphic or video is shown in substantially the centre of the display, and then target graphics or video are shown at different positions on the display about the centre. A test subject is positioned in front of the patient display a known distance therefrom, and a camera captures an image of the test subject's eyes, to allow gaze direction determination to be performed. The captured images are displayed to a clinician user by a controlling test application, the clinician making a determination based on the images as to whether the test subject saw a target graphic or video when it was displayed. The clinician user then makes an appropriate input into the controlling test application, which also logs the position at which the target image was displayed. By displaying target graphics at multiple locations on the screen and logging the clinician inputs, the controlling test application is able to build up a plot of the peripheral vision field of the test subject. This plot can then be graphically displayed to the clinician user, and stored with the test results for future clinical use.

In one example of the invention the fixation graphic and the target graphic is video content, which continues playback when displayed as a fixation graphic, and subsequently as a target graphic. In this way, a child subject's attention can be maintained as the video content playback is continued irrespective as to whether it is shown as the fixation graphic or a target graphic, and hence the story represented by the video content is not interrupted. The particular video content is selected by the clinician user so as to appeal to the particular child test subject.

In another example of the invention a visual perimetry test is dynamically adapted during the running of the test by adding in additional test points in dependence on whether the test subject has seen the points. The determination as to whether the test subject has seen a test point may be performed by a user or automatically using image processing algorithms operating on video imagery of the test subject. Howsoever such a determination is made, in this example the test is dynamically adapted by adding in an easier test point into the test at which a target graphic or video is to be shown. The easier test point is added in such that it is located closer towards the centre of the test subject's vision i.e. has a smaller angular magnitude with respect to the central line of sight of the test subject. The added test point may then be displayed to the user immediately after been added, or may be displayed to the user later, after other test points at different angular positions have been shown. In the latter case the continuity of the test is maintained, and the test subject should not experience any long gap between seeing test images that may cause the subject to wander their eyes around the screen.

In view of the above from one aspect an example of the invention provides a peripheral vision measurement system, comprising: a first video display arranged to display test images to a test subject; a camera arranged to capture images of the test subject; a second video display arranged to display captured images of the test subject to a user; and one or more processors arranged to control the first and second video displays, and having at least one input arranged to receive feedback data from the user relating to the displays; wherein the feedback data relates to a judgment by the user as to whether the test subject has seen a test image when displayed on the first video display, said feedback data being recorded against the position of the test image when displayed on the first video display, whereby to collate measurement data indicative of the peripheral vision field of the test subject.

From another aspect an example of the invention also provides a peripheral vision measurement system, comprising: a subject video display arranged to display test images to a test subject; a camera arranged to capture images of the test subject; a user video display arranged to display captured images of the test subject to a user; and one or more processors arranged to control the subject and user video displays, the user display being controlled so as to be augmented with at least one indicator relating to the position of a test image on the subject display.

In one example the at least one indicator is positioned in the user display at a corresponding position to the position of a test image in the subject display. The corresponding position may take into account the direction of view of the camera to the test subject. In particular, the corresponding position of the at least one indicator on the user display may be translated in the plane of the display in dependence on the displacement of the camera position from the central gaze direction of the subject.

From a further aspect an example of the invention provides a peripheral vision measurement system, comprising: a first display device arranged to display a fixation image to a test subject, and to intermittently display a plurality of test images; and a processor arranged to collate data relating to whether the test subject saw a test image at a particular location on the first display device, whereby to measure the peripheral vision field of the test subject; wherein the fixation image and the test images are video images, playback of at least part of the content of the video images being substantially continuous between the fixation image and the test images.

From a yet further aspect another example of the invention provides a peripheral vision measurement system, comprising: a first display device arranged to display a plurality of test images to a test subject at different positions on the display; a processor arranged to control the first display device to display the plurality of test images at the different positions, and to use a determination as to whether the test subject has seen a particular test image at a particular position; wherein the processor is further arranged to calculate the position of an additional test image to be shown to the user at a related position to the particular position of the particular test image in dependence on the determination, the related position being closer to the test subject's line of sight than the particular position, and to control the first display device to display the additional test image at the related position.

Within one embodiment of the above the related position at which the additional test image is displayed has substantially the same or similar rotational angular position as the first test image, and a smaller angular magnitude. In addition, within one embodiment at least one second test image at a different rotational angular position to the first test image is displayed to the user before the additional test image. With such an arrangement, the test subject does not become aware that test points are being added in to the test, as there is no unusually long gap between the subject perceiving test images.

Another aspect of the invention provides a peripheral vision measurement method, comprising: displaying test images to a test subject; capturing images of the test subject; displaying the captured images of the test subject to a user; and receiving feedback data from the user relating to the displays; wherein the feedback data relates to a judgment by the user as to whether the test subject has seen a test image when displayed on the first video display, said feedback data being recorded against the position of the test image when displayed on the first video display, whereby to collate measurement data indicative of the peripheral vision field of the test subject.

Further features, aspects, and examples of the invention will be apparent from the appended claims.

BRIEF DESCRIPTION OF THE DRAWINGS

Further features and advantages of the present invention will be apparent from the following description of embodiments thereof, presented by way of example only, and by reference to the accompanying drawings, wherein like reference numerals refer to like parts, and wherein:

FIG. 4 is a diagram illustrating a patient screen in the first embodiment of the present invention;

FIG. 5 is a drawing illustrating a clinician view in the first embodiment of the invention;

FIGS. 6(a) to 6(d) are a sequence of drawings illustrating the operation of the first embodiment of the present invention;

FIG. 7 is a block diagram of the components of a second embodiment of the present invention;

FIG. 20 is a flow diagram illustrating part of the operation of the second embodiment;

FIG. 21 is a flow diagram illustrating another part of the operation of the second embodiment;

DESCRIPTION OF SPECIFIC EMBODIMENTS

Various examples of the invention will now be described with respect to the accompanying figures.

Figure 1:
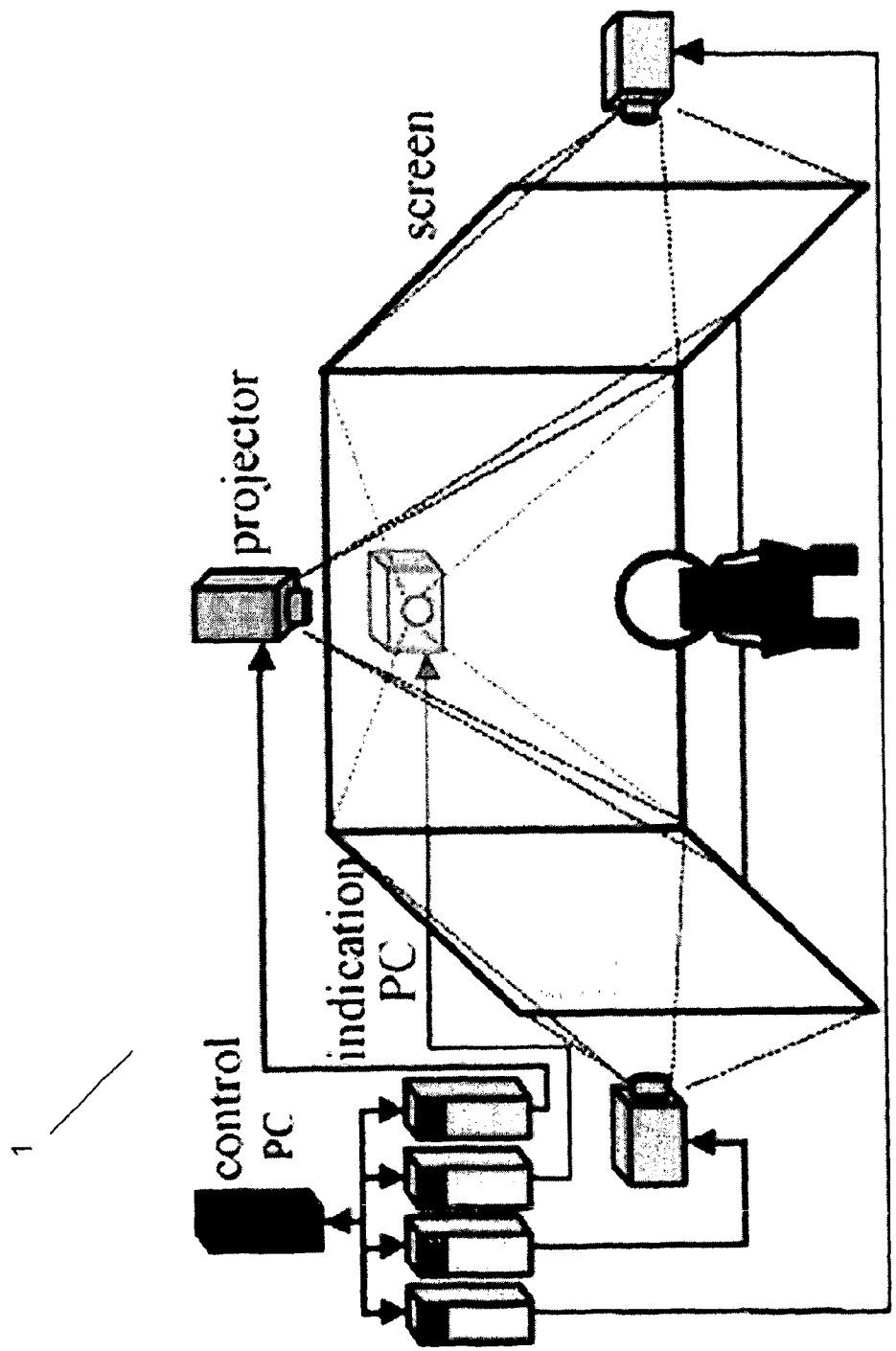
FIG. 1 is a diagram of a perimetry measurement system of the prior art.
Figure 2:
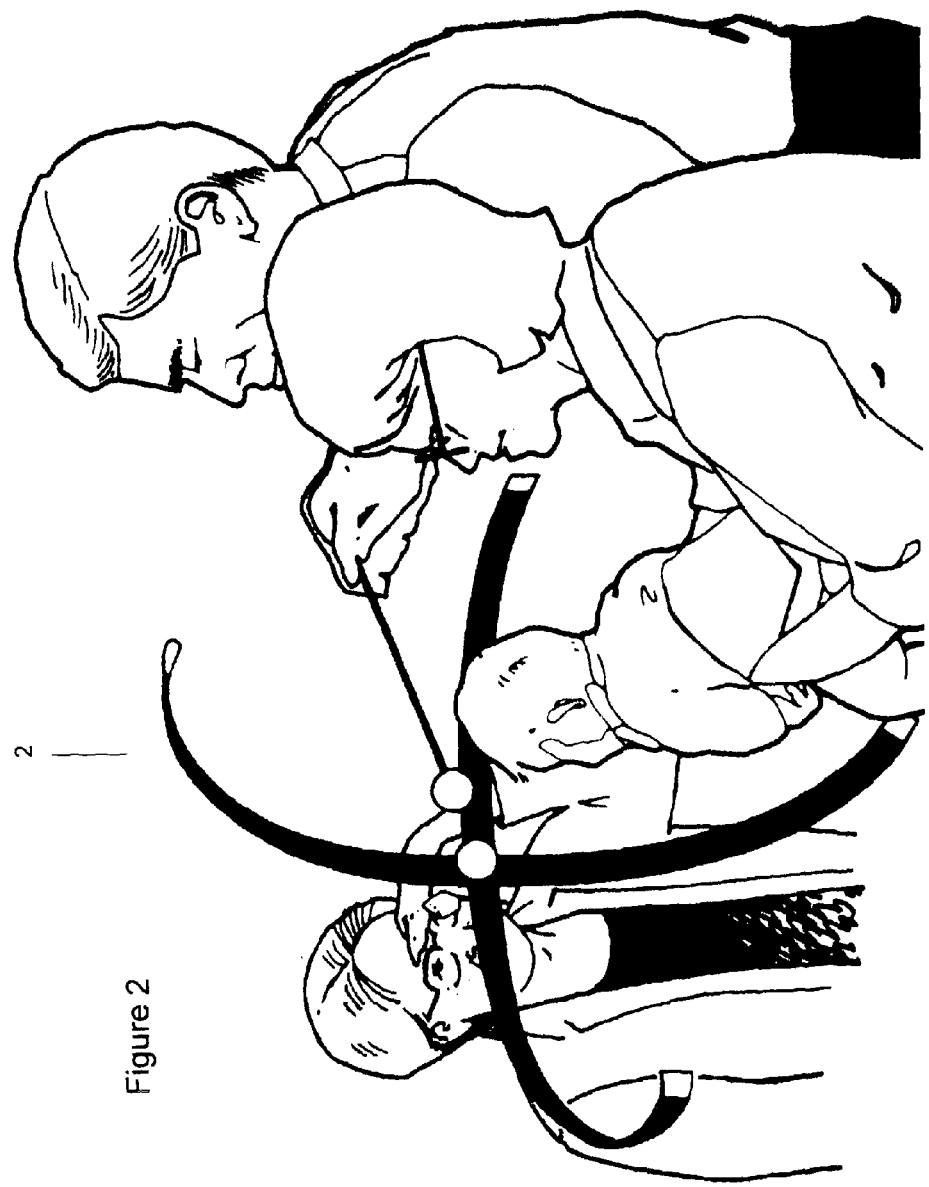
FIG. 2 is a drawing illustrating a perimetry measurement technique of the prior art.
Figure 3:
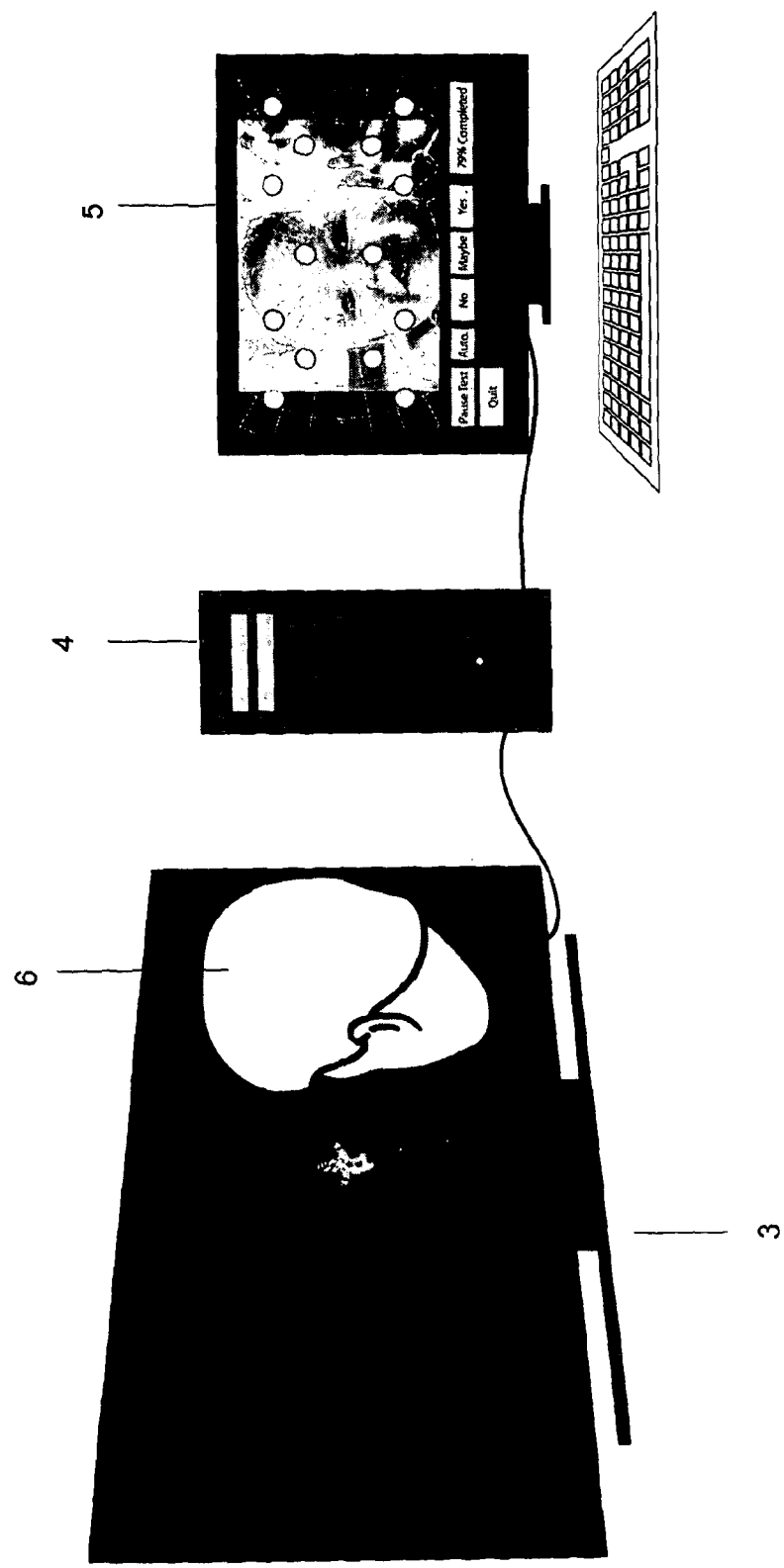
FIG. 3 is a diagram illustrating the components of a first embodiment of the present invention.

A first example embodiment of the invention is shown in FIG. 3. Here, a visual perimetry measurement system 10 comprises a patient display screen 3 in front of which a test subject, in this case a small child 6, is positioned. A clinician display screen 5 is also provided. A controlling computer 4 controls the images displayed on both the patient display 3, and the clinician display screen 5. The controlling computer 4 is provided with a suitable software program and corresponding hardware, in order to cause displays to be produce on the patient display screen 3, and the clinician display 5. In addition, the controlling computer 4 also receives feedback from the clinician display screen 5, for example through a mouse or keyboard interface to allow a clinician to select buttons displayed on the clinician display, as will be described. Also provided as part of the system, but not shown in FIG. 3, is an image capture device such as a camera, which is positioned so as to catch a frontal facial view of the subject 6, whilst the subject 6 is looking at the patient display screen 3.

FIG. 4 illustrates the patient display in more detail. One of the main problems with performing visual perimetry tests on young children is that young children often cannot concentrate on a fixation point for long periods of time. To overcome this problem, in the present example embodiment a central fixation graphic 32 is displayed in the centre of the patient display screen 3, the graphic being chosen so as to be entertaining to a young child subject. For example, the graphic may be a still graphic or an animated graphic, or may, in alternative examples, be, for example, video output, the content of the video being a popular children's' television program, and preferably one already known to the test subject.

In order to provide for testing of a child's peripheral vision whilst the child is fixated on the central fixation point 32, a target graphic or animation 34 is also provided, intermittently shown at various test points on the screen, as determined by the control computer 4. The test graphic may be an animated graphic, or may, alternatively, be a video graphic, such as described previously in respect of the fixation point.

The fixation graphic 32 may be permanently displayed in the middle of the screen, or, in alternative examples, may be only intermittently displayed, for example it not being displayed when a target graphic is being displayed. Likewise, the target graphic 34 is intermittently displayed at different locations. The camera (not shown) captures images of the subject's face from a full frontal perspective, and these images are provided, via the control computer 4, to the clinician display 5, such that the clinician can determine the direction of gaze of the child subject 6.

FIG. 5 illustrates one example of the clinician display 5. In particular, the clinician display 5 presents a video display 50 formed from the video image captured by the camera (not shown) of the child subject 6's face when looking at the patient screen 3. The video image is overlaid by a measurement graticule 51, on which are marked test points, illustrating the location of test points at which the target graphic 34 will appear on the patient display 3. For example, test points 52 illustrate locations at which the target graphic will appear, or has appeared, in the past. The colour (or, in other examples, some other characteristic, such as the shape) of the test points 52 can alter depending on whether the target graphic has been shown at those points, and whether the child subject noticed the target graphic at that point, as will be described later.

The clinician display 50 also includes a number of clinician feedback and control buttons. In particular, "pause" and "quit" control buttons are provided, which when selected by the clinician for example with a keyboard or mouse cause the test to be paused or to end. During the test, the main buttons that the clinician will use are the "no" button 54, the "maybe" button 56, and the "yes" button 58. To use these buttons the clinician monitors the video image of the child in the clinician video display 50, and detects whether the child's direction of gaze moves towards the location of the test point at which a target graphic is presently being displayed. As will be discussed, the location of the test points 52 are shown on the clinician display, and a colour coding system illustrates to the clinician which test points are being shown, which are about to be shown, and which are presently being shown. Based on this information, the clinician makes an estimate using the "no" button 54, "maybe" button 56, and "yes" button 58 as to whether the child subject has noticed the target graphic.

More particularly, if it is clear that the child subject has not noticed the target graphic at the present test point being displayed, then the clinician selects the "no" button 54. If it is possible that the child noticed the target graphic, but the clinician is not sure, then the clinician selects the "maybe" button 56. In this case, the test point is maintained within the test list, and the target graphic is shown at the same test point again later in the test. If, on the other hand, the clinician determines that the child does spot the target graphic, and that the child's line of gaze moves to the graphic, then the clinician selects the "yes" button 58. Depending on the clinician's responses using the "no", "maybe", and "yes" buttons, the clinician's feedback is logged with respect to the target points, and the control computer 4 is then able to build a graphical map of which targets were spotted by the child and which targets were not. As such, a perimetry map of the child's peripheral vision can be obtained.

Moreover, the number of respective "yes", "no" or "maybe" decisions made by the clinician may be logged so as to build up over time statistical data from which the probability of detection and confidence measures can be found. In particular the probabilities of detection can depend on the number of 'yes' responses as a proportion of all responses, per target. These probabilities can then be used to refine the test in future, to elaborate for instance on the detectability of certain targets.

FIG. 6 illustrates the operation of the clinician's video display 50 in more detail. In particular, assume that FIG. 6*a* shows the start of a test in progress. The circles on the clinician display show the target graphic locations that will be displayed to the child. These circles can be colour coded so as to indicate to the clinician whether the target graphic is presently being shown at one of the locations, whether it has been shown at the location, and whether it is about to be shown at the location. Additionally colour coding can be used to further indicate, if the target graphic has been shown at the location, whether the child saw the target at that location, or not. Starting at FIG. 6(*a*), target point 62 is colour coded such that it indicates to the clinician that the target graphic is presently being shown at this location. All other target points other than target point 64 are colour coded to show that they are still to be tested. Target point 64 is colour coded with a different colour to indicate that this is the next target point that will be shown, after target point 62. At the present point in the test as depicted in FIG. 6(*a*), therefore, the child patient screen is showing the target graphic at the position of target point 62, and the target graphic will then next be shown at the position of target point 64, and all other target points are positions at which the target graphic will be shown later in the test.

Next assume that the clinician determines that the child's gaze moves to the target graphic located at the target point 62. In this case, the clinician can select the "yes" button which then becomes highlighted, as shown by highlighted yes button 66 in FIG. 6(*b*). The control computer 4 logs the clinician input that the child noticed the target graphic at the location of target point 62. The clinician display also shows that the next target point at which the target graphic will be displayed is at location of target point 64.

Once the positive "yes" response has been logged, the clinician display then proceeds to that shown in FIG. 6(*c*). Here, the colour of target point 62 has changed, to a colour that indicates that this target point has already been displayed. For example, the colour of the target point may change to blue. When a target point is being displayed, it may be shown as green. A target point that is to be displayed next may be shown as red, and, when it is about to be displayed, as amber. In this case, the target point 64, which is the next target point to be displayed, changes to amber, to inform the clinician that the target graphic is about to be shown at that point. The clinician can then prepare him or herself to check whether the child subject's gaze moves to that point, when the target graphic is shown at the point.

In FIG. 6(*d*) the colour of target point 64 changes to green, to show that the target graphic is at that moment presently being shown to the child subject 6 on the patient display 3 at the position of target point 64. Target point 62 remains a blue colour, to indicate that it has already been shown. The display then moves around in a cycle back to FIG. 6(*a*), with another of the target points changing to red to indicate that that point will be the next target point to be displayed. During this time period the clinician makes a decision as to whether the child noticed the target graphic when displayed at target point 64, and selects the appropriate input button. The clinician display then subsequently cycles through these several states with the clinician inputting "yes", "no", or "maybe" for each test point, until all of the points have been tested.

It is important during a perimetry test that the child's attention is brought back to the fixation graphic in the centre. Thus, once the target graphic has been shown at a particular target point, and the physician's input has been received as to whether the child has noticed the target graphic, the target graphic is removed from the screen, and the fixation graphic placed back into the middle of the screen, to draw the child's attention back to the middle. Thus, during the state shown in FIG. 6(*c*), where the target point 64 is displayed as amber to warn the physician that the target graphic is about to be displayed at this location, the patient screen 3 displays the fixation graphic 32 in the centre of the screen, so as to bring the child subject 6's attention to the centre point of the patient display screen 3. In this way, the child's gaze is returned to the centre of the screen, such that when the target graphic is placed onto the screen at a new position, a proper test of the child's peripheral vision can be performed, for that particular target graphic position.

Figure 19:
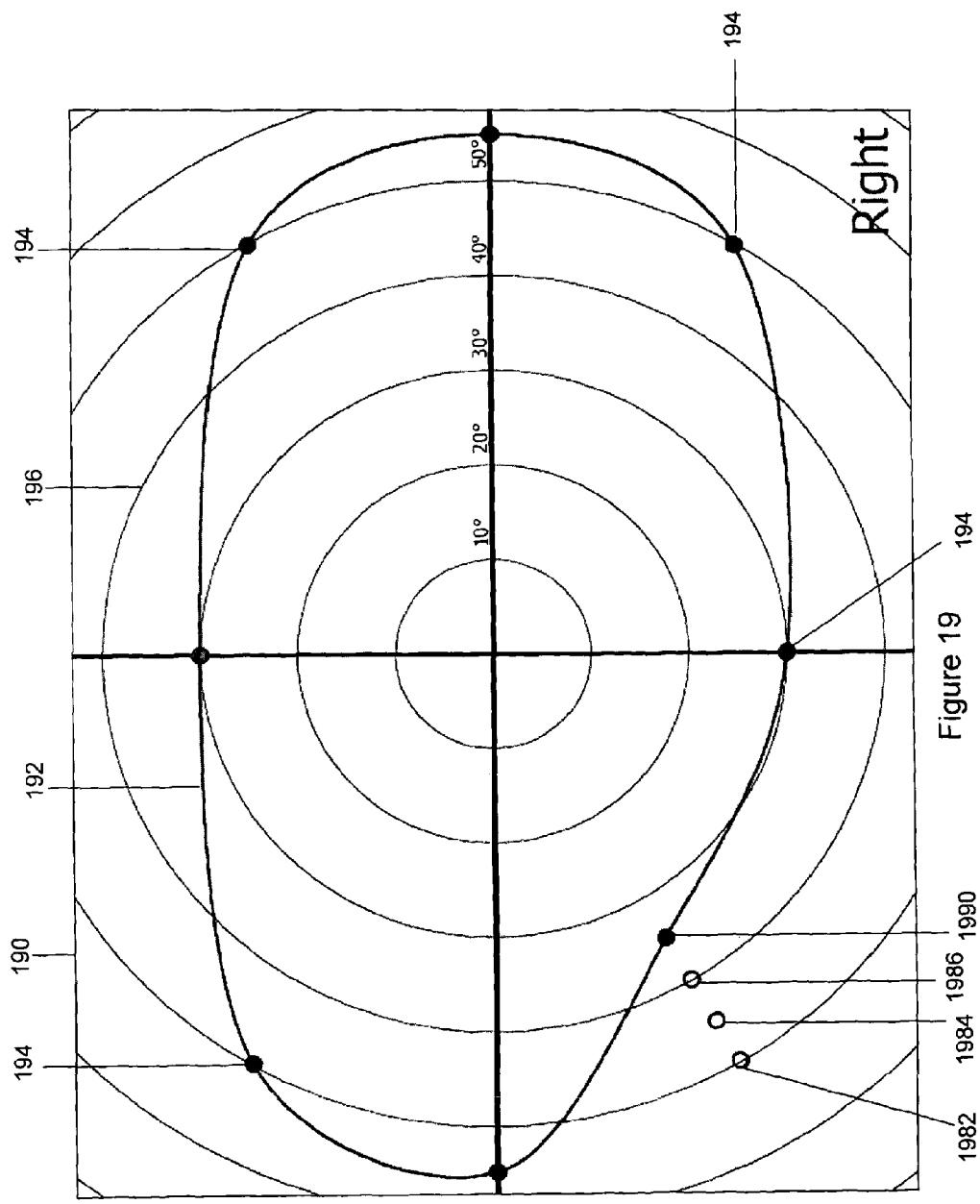
FIG. 19 is a perimetry plot obtained by the measurement system of the second embodiment.

As mentioned, as the test proceeds, the control computer 4 logs which target points are spotted by the child, and which are not. This then allows the computer to build a perimetry plot, showing the extent of the child's peripheral vision, as determined by the test. An example perimetry plot, being a plot produced by the second embodiment to be described next, is shown in FIG. 19, although it should be understood that the first embodiment of the invention presently described would produce perimetry plots in a similar format.

Using the example first embodiment, therefore, visual perimeter testing of small children can be undertaken in a reliable and controllable manner. By using an animated graphic or video as the fixation point, and/or the target point, the child's attention can be maintained on the test. Moreover, the test environment is friendly to the child, as the child does not need to place their head into an enclosed space, such as with the Goldman or Humphreys test apparatus of the prior art. Likewise, the fixation point of the child is selected so as to be of interest to the child such that the child will naturally fixate on the fixation point. The same is also true of the target graphic, in that the target graphic is chosen so as to be of interest to the child, such that when the target graphic is shown the child is motivated to look at the graphic.

From the clinician's perspective, the first example of the invention provides a repeatable and controllable test environment for visual perimeter tests to be conducted. Information capture and logging is readily performed by the control computer 4, based on the clinician input. The augmented clinician video display, having the view of the child's face augmented by an indication as to where the target graphic is about to be shown on the patient screen helps the clinician to determine whether or not the child's gaze moved to the target graphic. In addition, precise placement of the target graphic is possible, thus allowing information about the child's visual field to be obtained as accurately as possible.

A second example embodiment of the invention will now be described with respect to FIGS. 7 to 25.

FIG. 7 is a block diagram of the second example embodiment of the invention. The second example embodiment builds upon the ideas previously described in respect of the first example embodiment, but adds several additional features in, as will be described.

The second example embodiment of the invention has the same system components as the first example embodiment described previously. That is, a controlling computer 72 is provided, which controls a clinician monitor 74 on which a clinician display image is displayed, and a patient monitor 76 is also provided, on which both fixation graphics 762, and target graphics are displayed. An image capture device in the form of video camera 78 is positioned substantially in the centre of the patient display screen 76, so as to capture a full frontal view of a child subject when the child subject is positioned in front of the patient display. Both the clinician display 74 and the patient display 76 are controlled by a dual monitor controller 728 in computer 72, the dual monitor controller 728 being, for example, a graphics card capable of controlling two monitors at the same time. An example graphics card suitable for the task is the nVidia GE Force FX5200 Graphics Chip, which provides two analogue outputs.

The camera 78 provides images to camera controller 726 in computer 72. The camera controller 726 may be a universal serial bus (USB) host, in which case the camera 78 may be a USB webcam or the like. The computer 72 further comprises a central processing unit 724 and associated components, to allow the computer to run the system control software, control the display on the monitors, and receive inputs from the clinician user. In this latter respect, a mouse and keyboard controller 730 receive control inputs from a mouse and/or keyboard, that are operated by the clinician user for example to select buttons on the graphical user interface provided by the clinician display 724.

As will be understood, the hardware elements of the computer 72, patient display 726, and clinician display 724 may be off the shelf components, provided that they meet some additional requirements, as described next.

In particular, with respect to the patient display 726, this should possess a high enough resolution to provide comfortable close viewing for the child subject, whilst being large enough that, at the distance at which the child subject is placed from the screen, the screen can display target graphics across the range of viewing angles that are required to be tested. Typically, the range of peripheral field view is 30° to either side in the horizontal plane, as well as in the vertical plane. A comfortable viewing distance is typically around 60 cm, although for child subjects a closer viewing distance can be tolerated. The screen size required is a function of viewing distance from the screen, and for a viewing distance of approximately 48 cm, a screen size of approximately 98 cm (42 inches) can be used. A suitable screen, therefore, is, for example, a 42 inch high definition plasma screen, such as, for example, the "Panasonic TH-42 PHD 8". Various other high definition plasma, LCD, or LED screens are readily available of the required size, which could also be substituted.

With respect to the clinician screen, the requirements are not as high. The clinician screen may be displayed on a standard computer monitor, such as a 19 inch monitor, or the like.

Figure 8:
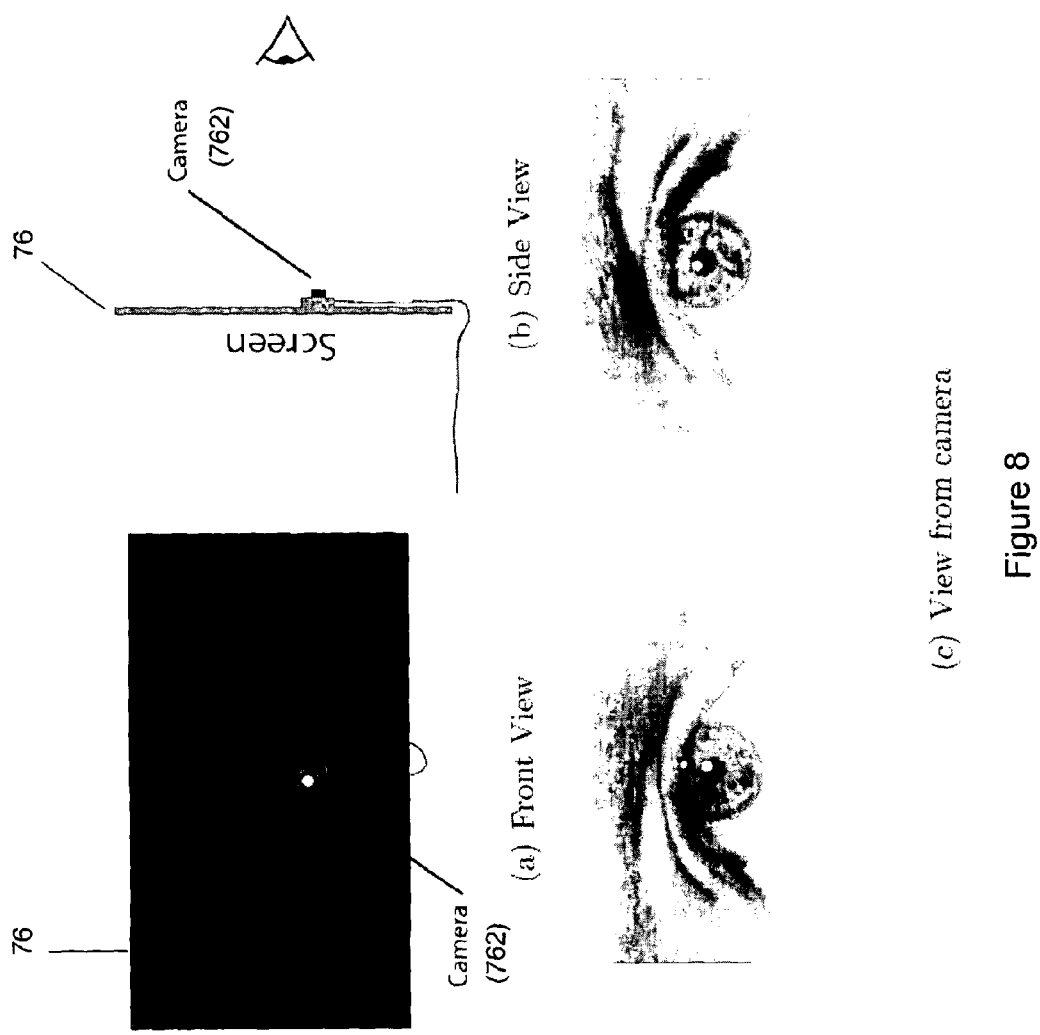
FIGS. 8(a) to 8(c) are drawings illustrating the arrangement of a camera and patient screen in the second embodiment of the invention.

As mentioned, the camera 762 is positioned in front of the patient display 76 and fixed to the screen, as shown in FIGS. 8(*a*) and (*b*). Rather than being positioned at exactly the centre of the screen, which is where the fixation target will be displayed, in the present example the camera is fixed to the screen just below the fixation point. This means, therefore, that when the child subject is looking at the fixation point the subject is not quite staring into the camera lens, but the difference in direction of gaze of the child subject looking at the centre of the screen and the image of such as captured by the camera is very small. FIG. 8(*c*) shows a view captured by the camera of a subject looking at the fixation point, and it will be seen that it appears as though the user is in fact looking directly at the camera. As such, changes in direction of gaze can be readily detected by the clinician.

In the above example the camera is placed as close to the centre of the patient display as possible, although not quite in the centre, as this is where the fixation image is to be displayed. However, the patient image obtained has the patient apparently looking at the camera sufficiently enough such it appears as if the patient is staring into the camera.

In another example, however, the augmented view can be further adjusted to compensate for the positioning of the camera with respect to the test subject, and the clinician view of the subject that is thus obtained, and in particular by altering the position of the target indicators on the augmented view such that they are translated on the augmented view in a direction opposite to the actual displacement of the camera from the optimal centre position.

For example, imagine that the camera is positioned at the bottom of the patient display, rather than substantially in the center. In this case, from the view point of the camera, when the test subject is looking at the fixation image in the center of the display it will appear as of the gaze of the subject is lifted upwards, within the top half of the clinician display. If the gaze of the subject were to move downwards to the bottom of the patient display, then at best from the view point of the camera it may appear as if the test subject is looking directly into the camera i.e. the gaze is centered in the augmented view. In reality, however, the subject gaze is directed downwards, with respect to the patient display. On the other hand, if the subject looks upwards from the fixation image towards an upper part of the patient display, from the point of view of the camera and the clinician display it will appear as if the subject's gaze moves even higher towards the top of the clinician display.

The opposite effects are of course obtained if the camera is positioned at the top of the patient display—the subject appears to be gazing downwards. The same effects in the horizontal plane are obtained if the camera is placed to the left or right of patient display. The effects also compound with each other—a camera placed at the bottom right hand corner will make it appear as if the test subject, when looking at the central fixation image will be gazing at the upper left part of the clinician display.

To compensate for camera positioning, therefore, the placement of the target indicators on the augmented clinician display can be adapted such that they appear at the position on the clinician view where it will appear, from the point of view of the camera looking at the test subject, that the subject will look if he or she sees the test image at the target location in the patient display. Generally, as noted this will involve a translation of the position of a target indicator in the augmented view in a direction opposite to the displacement of the camera from the ideal center position (or, more generally, from the fixation image position).

For example, if, as noted above, the camera is located at the bottom of the patient display, in the middle, then the subject central gaze (i.e. when looking at the center of the patient display) will appear in the clinician view to be raised into the upper half of the clinician view. Therefore, a target indicator in the augmented display corresponding to a test target in the patient display located in the middle horizontal plane of the patient display should be displaced upwards in the augmented clinician display into the upper half of the clinician display. Likewise, a target indicator in the augmented display corresponding to a test target in the patient display located at the bottom of the patient display should be displaced upwards in the augmented clinician display towards the middle of the clinician display. Similarly, a target indicator in the augmented display corresponding to a test target in the patient display located at the top of the patient display should be displaced right at the top of the augmented view in the clinician display.

It will be understood that similar displacements of the target indicators in the augmented view in the opposite direction from the displacement of the camera would also occur if the camera is located at the top of the patient display, or to the left or right of the display. Moreover, the displacement can also be combined i.e. if the camera is located at the bottom right corner of the display then the target indicators are displaced upwards and to the left in the augmented display.

The amount of displacement of the target indicators required depends on the displacement of the camera from the optimal central position. Various linear or non-linear scaling factors can also be applied to calculate the displacement.

In order to control the hardware components just described, the computer 72 is provided with a computer readable storage medium, such as a hard disk drive 732, on which is stored software which when executed by the CPU 724 causes the computer to display the clinician video display on the clinician display 74, and the fixation and target images on the patient display 76, as will be described in more detail. Additionally, the software enables the computer 72 to receive feedback from the clinician via the mouse and keyboard, to enable the clinician user to interact with the graphical user interface provided by the clinician video display. The software has several modules, and makes use of different sets of stored data, as will be described next.

A first software module to be stored on hard disk 732 is the clinician view module 7326. The clinician view module is responsible for running the entire application, and causes the clinician video display, including the clinician graphical user interface, to be displayed on clinician display 74. Further details of the clinician video display, and the clinician GUI, will be given later. However, the clinician view module 7326 is responsible for providing the main elements of the GUI, and in particular in enabling the clinician to enter patient details, accessing patient records including records of previous tests, so that these can be displayed to the clinician, and providing GUI control buttons to enable and capture clinician feedback during tests. Clinician view module 7326 also controls the output of the video display captured by the camera 78 during a test, and controls, together with the test module 7340, the running of a test, for example to indicate to the clinician where a target graphic is next going to be displayed on the patient display.

A second software module is the child view module 7330. The child view module 7330 interfaces with the clinician view module 7326, and acts under the control of the clinician view module 7326. The main task of the child view module 7330 is to control the images displayed on the patient display 76. The child view module 7330 accesses stored content, stored as themes 7322, which are content for the fixation and target graphics. As discussed previously, the fixation and target graphics may be animated graphics, or may, preferably, be video content, such as children's' television programs, or the like. This content is stored categorised by "themes", on the hard disk 732, as the themes records 7322. An example "theme" may be a popular children's' television show, such as, for example, "In The Night Garden". Various different "themes" can be stored as theme records 7322, for example different sets of content for use with boys and girls, or for children of different ages. Whatever content is used, the child view module 7330 accesses the content, and controls the patient display 76 to display the content at the fixation point, and at the target points, as directed by the clinician view module 7326. In this respect, the clinician view module 7326 may pass test plan data to the child view module, specifying the positions at which the target graphic should be displayed, as well as other settings relating to the display, such as, for example, whether the fixation graphic should be displayed at the same time as the target graphic, or not.

Additionally provided is a patient class module 7332 which provides methods that store all of the patient's details along with lists of their previous tests. It also provides access to this data as well as providing functions which work on that data, such as age calculations. In particular the patient class module 7332 accesses patient record data 7324, with a separate patient record being stored for each patient that is tested, indexed by a patient ID. The clinician view module 7326 therefore delegates the task of managing patient records to the patient class module 7332. That is, when the clinician view module is controlled by the clinician to load patient details, the clinician view module passes the patient ID received from the clinician to the patient class module 7332, which then accesses the appropriate patient record, processes that record, and passes back display data to the clinician view module 7326, to be displayed on the clinician display 74.

The point class module 7334 is a further software module that contains methods that control information about each test point in a test, including position of a test point in terms of angle from the horizontal and vertical, and angle of magnitude. Each test point is stored as a test point object, controlled by the point class modules 7334. The clinician view module 7326 therefore works with the point class module 7334 to determine at which point the target graphic should be displayed next, and to control the clinician view to indicate to the clinician where a point is to be displayed. Likewise, the clinician view module passes back data received from the clinician (i.e. yes, no, or maybe), as to whether the point was recognised by the user, which is stored against the point by the point class module.

Additional modules include the settings module 7336, and a session settings module 7338. The session settings module 7338 provides a GUI to allow various settings of the application to be set by the clinician user, which settings are then stored by the settings module 7336. The session settings module 7338 also contains default settings, which are used by the application under the control of the clinician view module 7326 when it is first loaded. During a particular session these settings may be changed, and stored in the settings module 7336, for example to change the application settings on a test by test basis. Various settings may be set by the clinician user, such as, for example, the size of the fixation graphic, the size of the target graphic, whether the "auto add points" function is enabled (auto add points will be described later), the interval at which points should be added by the auto add function, whether the fixation graphic should be shown at the same time as the target graphic, whether in the case of a video target the video should be looped, whether random video content should be used, whether the target graphic should be automatically hidden after a preset amount of time of being displayed, etc.

In addition, various hardware settings may also be set, including display resolution settings of both the patient and clinician displays, as well as settings such as screen size of the patient display, and the distance from the screen that the child subject is placed. The settings module 7336 and session settings module 7338 allow all of these settings to be altered by the clinician.

A further module is the test module 7340. The test module contains all of the information required for a peripheral vision field test. This includes a list of the points tested and other information required for calculating the results. This module is in charge of managing the test as it is run, for example providing a test point that still needs testing to the main interface. The auto add function is also part of the test module 7340. The test module 7340 works closely with the point class module 7334 so as to actually run peripheral vision tests, comprising multiple points controlled by the point class module 7334. The test module 7340 is therefore called by the clinician view module 7326 when a test is to be run, and which then delegates the management of the test to the test module 7340. The module 7340 then calls various data and information relating to specific test points from the point class module 7334 and passes data back to the point class module 7334 during a test. Together, therefore, the clinician view module, point class module, and test module contain all of the data and methods necessary to run a test.

Finally, a "template maker" module 7328 is provided. This allows a clinician user to specify test point locations to create a new test profile. That is, the template maker module 7328 causes a target graticule to be displayed on the clinician display 74, and allows the clinician to select points on the graticule which will then form test points at which the target graphic will be displayed. The collection of points or metadata relating thereto can then be stored as a new test template, for use by the test module 7340. Likewise information regarding the specific points that make up the test are stored as point objects that are used by the point class module 7334.

Figure 9:
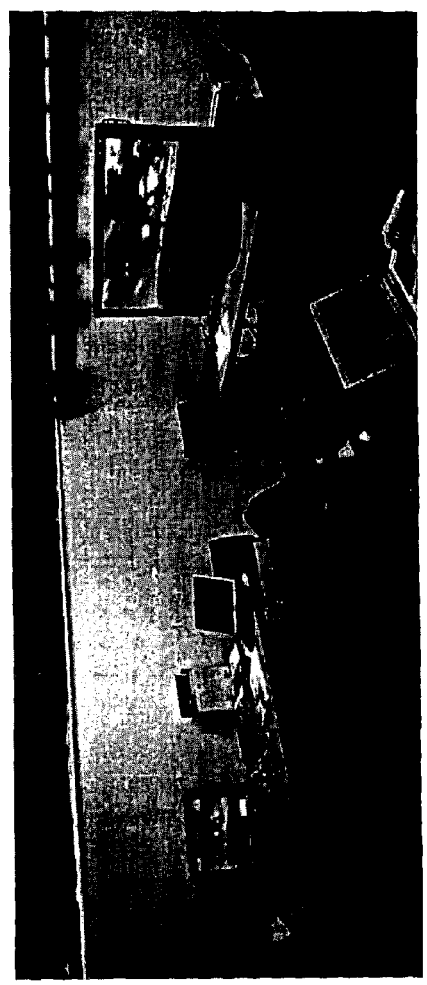
FIG. 9 is a photograph illustrating the system set up of the second embodiment of the invention.
Figure 11:
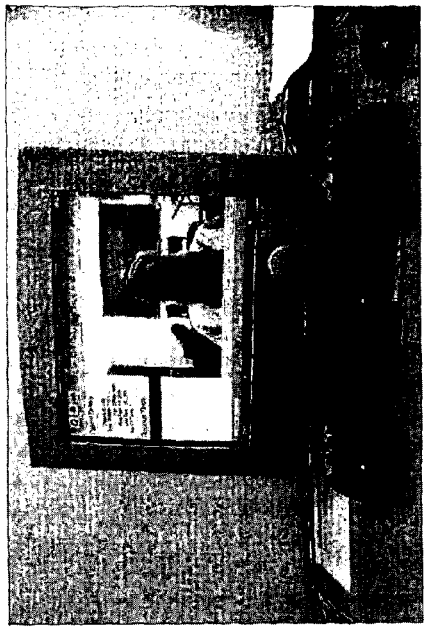
FIG. 11 is a photograph illustrating the clinician screen in the second embodiment of the invention.
Figure 10:
FIG. 10 is a photograph illustrating the patient screen in use in the second embodiment of the invention.
Figure 12:
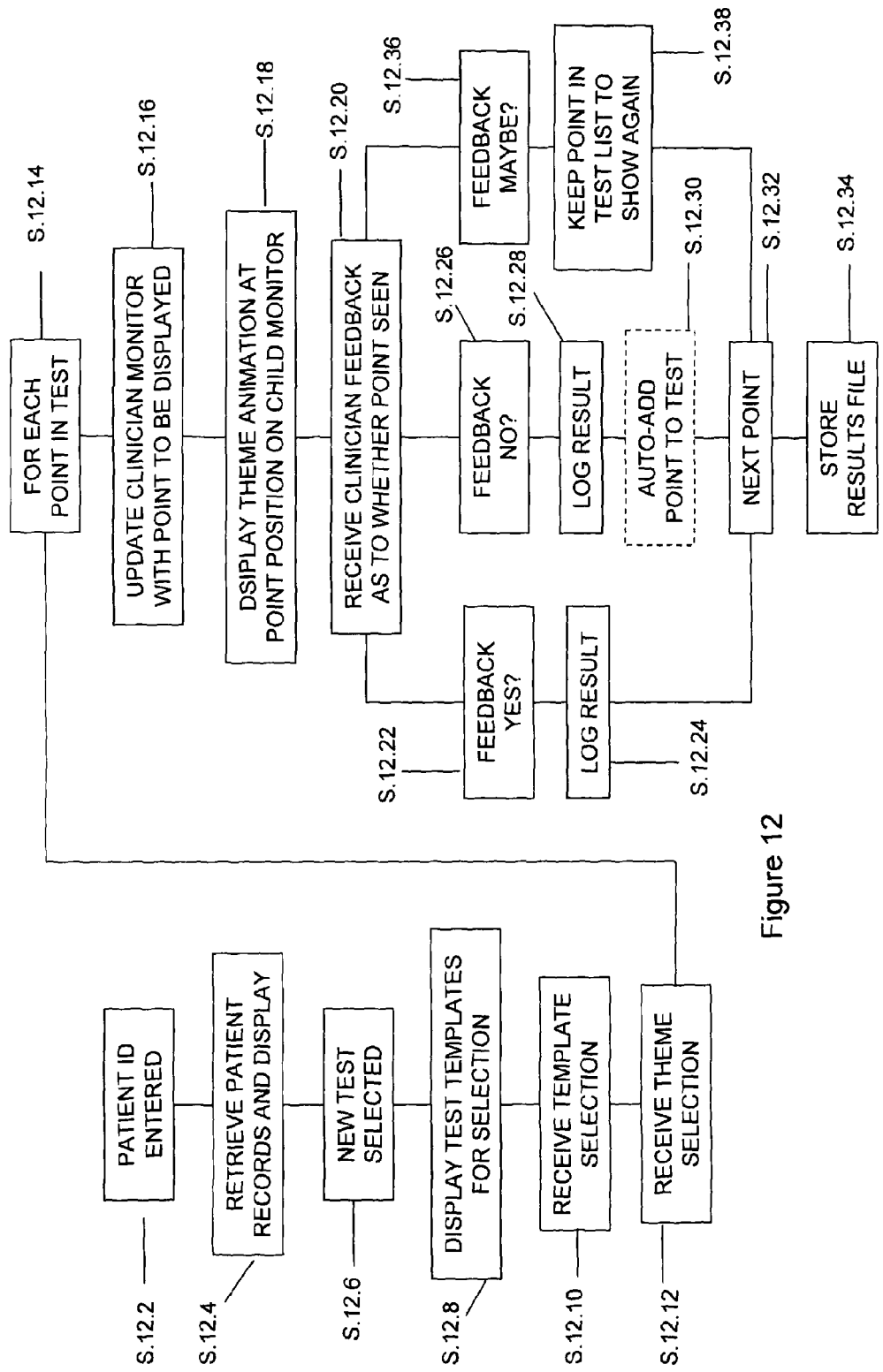
FIG. 12 is a flow diagram illustrating part of the operation of the second embodiment of the invention.

FIGS. 9, 10 and 11 show a peripheral vision testing system of the second example set up and ready to be used. In particular, FIG. 9 is a photograph of the testing room, with the patient display shown on the right, and the corresponding clinician display shown on the left. FIG. 10 illustrates a test subject placed in front of the patient display, and FIG. 11 is a photograph of the clinician display taken at the same moment in time as when the photograph in FIG. 10 was taken.

Having described the hardware and software of the perimetry measurement system of the second example, the operation of the system in performing a test will now be described with respect to FIGS. 12 to 19.

Figure 13:
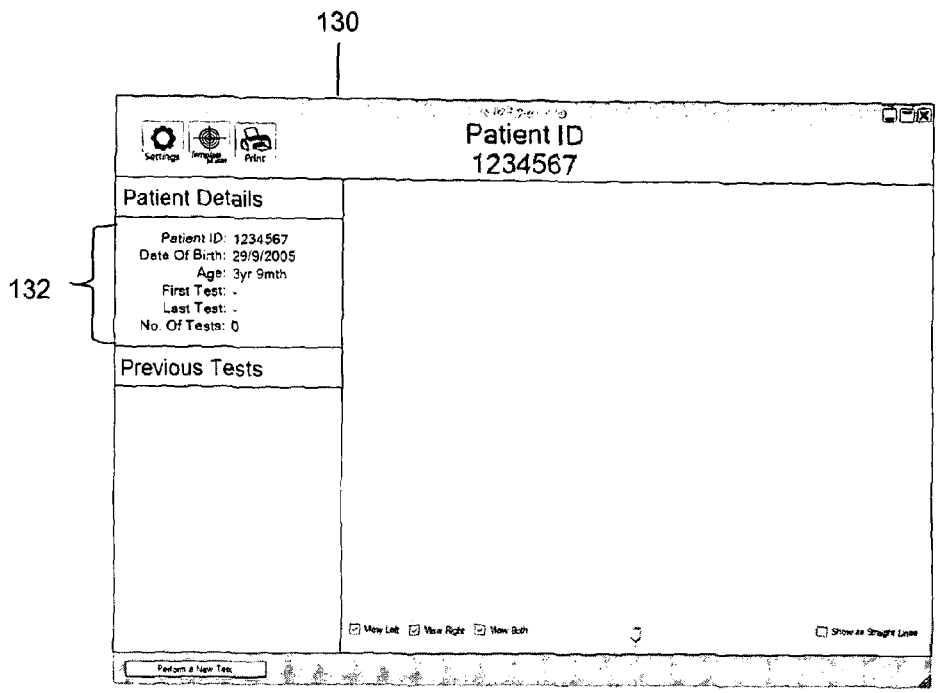
FIG. 13 is a screen shot from the clinician screen in the second embodiment of the invention.
Figure 14:
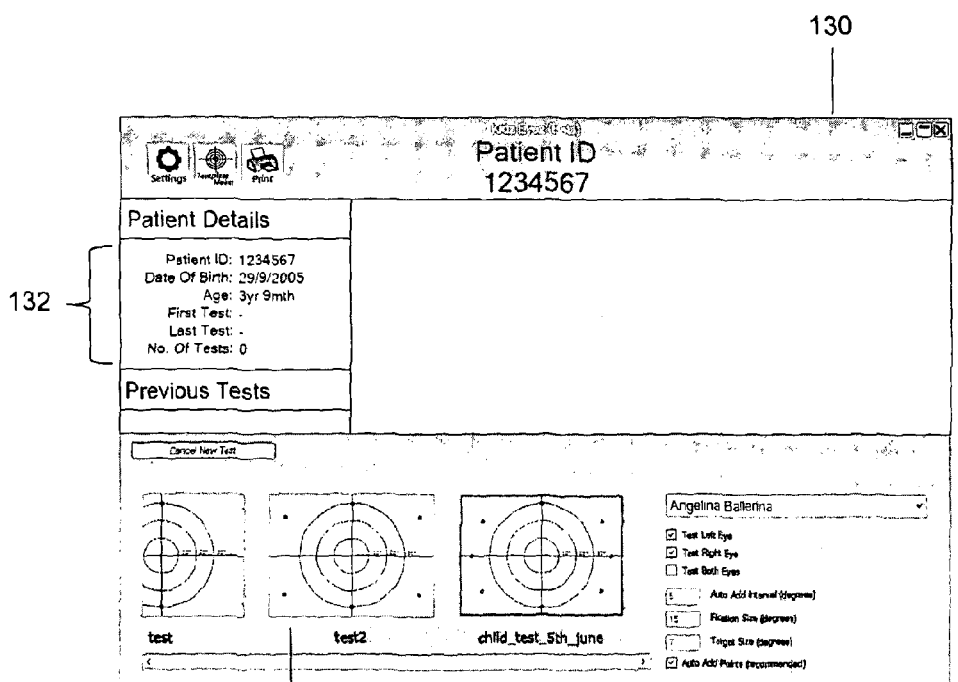
FIG. 14 is a further screen shot of the clinician screen in the second embodiment.

To operate the system the computer 72 is first booted up, and the measurement application started. When the application starts, it displays an input box to the clinician user, to ask for the patient ID of the present patient to be tested to be entered. The clinician then enters this information, and the clinician view module 7326 asks the patient class module 7332 to access the appropriate patient record (or to create a patient record if none is available). The clinician view module 7326 then displays the clinician graphical user interface 130 as shown in FIG. 13, having the retrieved patient details 132 included in a box on the left hand side. With respect to FIG. 12, these steps are performed at steps 12.2 and 12.4. Therefore, after step 12.4, the clinician display 74 displays the clinician graphical user interface 130 in the form as shown in FIG. 13.

Next, the clinician determines at step 12.6 that a new test is to be performed and therefore clicks the "perform the test" button provided by the GUI 130 on the screen. This then brings up a list of test templates, as shown by templates 134 in FIG. 14. This is performed at step 12.8. The test templates are either predetermined test templates provided with the application, or may be templates which the clinician has previously created, using the template maker module, described in more detail later. The clinician user then selects a template to be used at step 12.10, specifying at the same time which eyes are to be tested. Before starting the test the clinician user should also ensure that the child subject has been placed in front of the screen, with the appropriate eye covered, being the opposite eye to the eye that is to be tested.

After selecting a test template, the clinician user also selects a theme appropriate to the child subject. As discussed previously, several different content themes are stored, which are appropriate for children of different sexes, and different ages. The clinician user should select a theme appropriate to the age and sex of the child subject. Once this has been achieved, then the test can commence.

Figure 15:
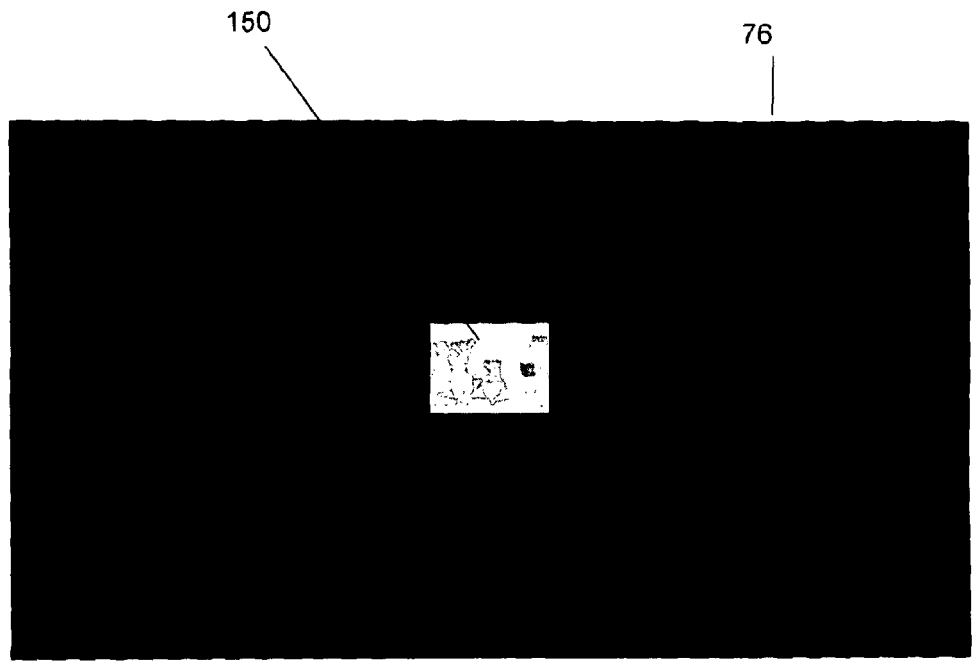
FIG. 15 is a first screen shot of the patient screen in the second embodiment.
Figure 16:
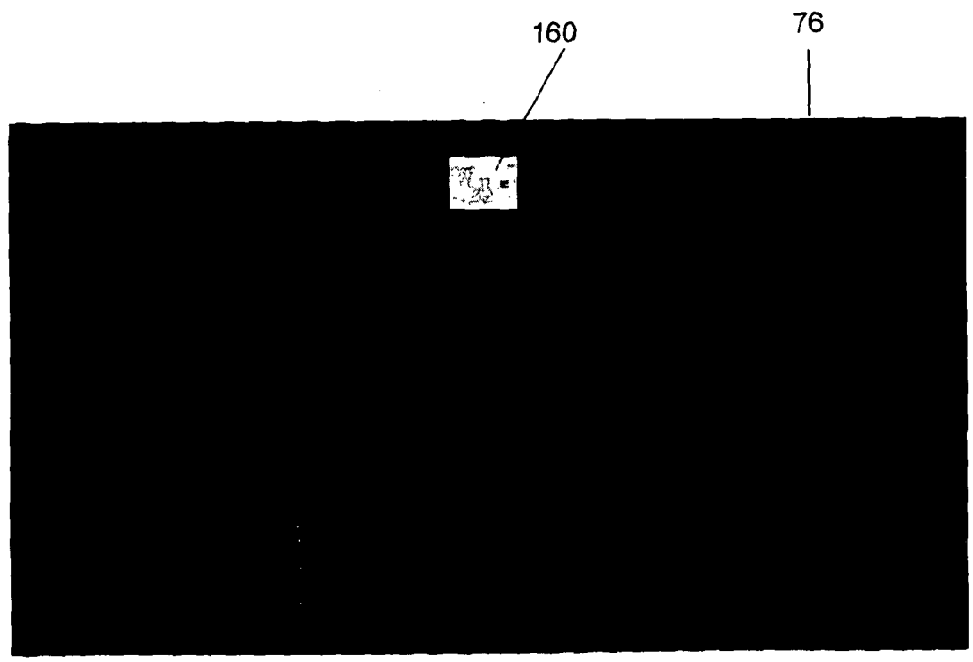
FIG. 16 is a second screen shot of the patient screen in the second embodiment.

As in the first example described previously, within the second example the test comprises showing the fixation target graphic or video to the child subject at the centre of the screen, and then intermittently showing a target graphic or video in a different position on the screen, and determining whether the child subject sees the target graphic. FIG. 15 illustrates the patient display showing the fixation graphic or video 150 in the centre of the screen. This is the "default" display, which brings the child subject's attention back to the centre of the display. When a target graphic or video is being shown, the display changes to that shown, for example, in FIG. 16, where the target graphic 160 is shown in this case above the fixation point. It will be understood that the target graphic 160 can be shown at any position on the screen, as defined by the test points in the test template.

Figure 17:
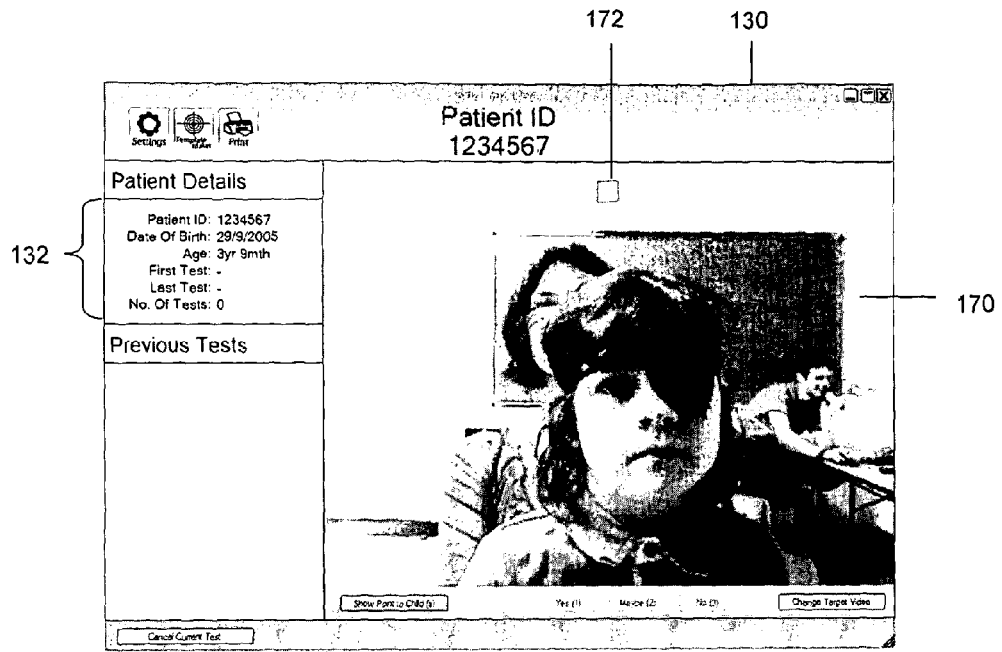
FIG. 17 is a further screen shot of the clinician screen in the second embodiment.
Figure 18:
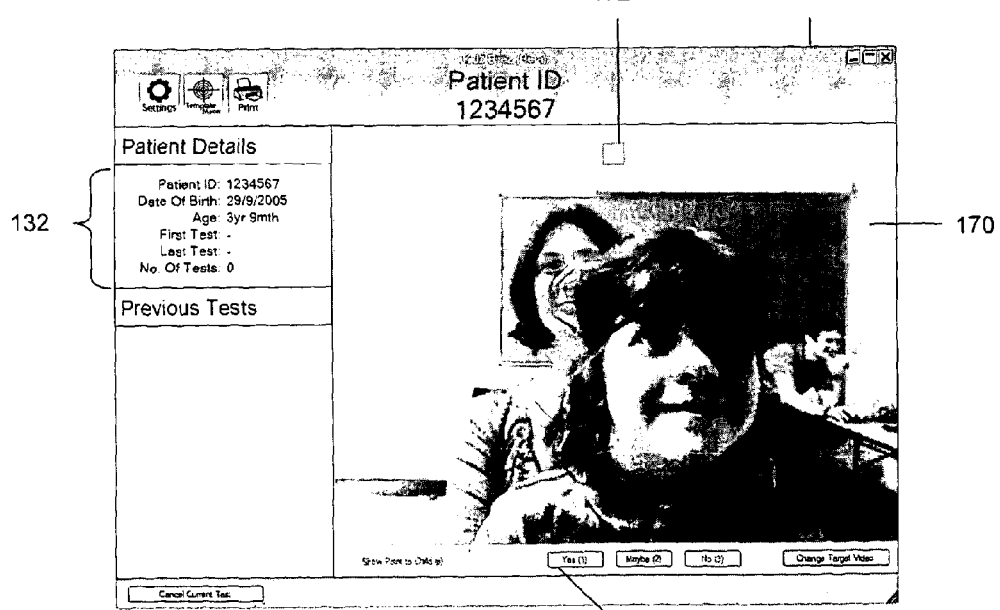
FIG. 18 is a further screen shot of the clinician screen in the second embodiment.

FIGS. 17 and 18 illustrate the clinician view during the test. FIG. 17 illustrates the clinician GUI 130, which has in the main window thereof the video image captured by the camera 78, of the child subject. In FIG. 17, the situation is that the fixation video or graphic is being shown at the centre of the screen, and hence it appears that the child is looking directly at the camera. However, the clinician display is also augmented by an indicator 172, which indicates to the clinician the position where the target graphic or video is about to be displayed to the child. The colour of the indicator 172 indicates whether the target graphic or video has been displayed at that position. For example, a red indicator 172 indicates to the clinician that the target graphic or video has not yet been shown to the child at that position, but is about to be shown to the child at that position. When the target graphic or video is then shown to the child at the indicated position, the colour of the indicator 172 changes, for example to green. This situation is shown in FIG. 18. Here, in comparison to FIG. 17 it can be seen that the colour of the indicator 172 has changed slightly, and also that the direction of gaze of the child subject has shifted to the direction of the position of the target graphic or video. In such a case the clinician can be relatively certain that the child has seen the target graphic or video, and hence the clinician is able to select the "yes" button 174, provided by GUI 130. It should be noted that the "yes", "maybe", and "no" buttons in the GUI only become available for selection during the period in which the target graphic or video is being displayed to the child, and not before. Thus, for example, in FIG. 17 the buttons are "greyed" out, whereas in FIG. 18 they are available for selection.

Returning to FIG. 12, the above described operations are repeated for every point in the test. That is, to perform a test firstly a processing loop is started at step 12.14, to ensure that each point in a test template is displayed. For each point in the test template at step 12.16 the clinician monitor is updated with an indicator 172 indicating where on the patient display the target graphic or video will be displayed. Thus, step 12.16 corresponds to the state shown in FIG. 17, described previously. Next, at step 12.18, the target graphic or video in accordance with the chosen theme animation is displayed at the present target point position on the child monitor. This therefore corresponds to the states shown in FIG. 16 for the patient display, and FIG. 18 for the clinician display. As the target graphic or video is being displayed, the clinician can feedback using the buttons 174 as to whether the child has seen the point. How the system next operates then depends on the clinician feedback.

More particularly, if the clinician selects the "yes" button 174, as shown in step 12.22, then the positive result is logged by the test module 7340, against the particular test point. Then, the next point can be processed, and the processing loop returns to step 12.16, for the next point. Alternatively, if the feedback is "maybe", obtained by the clinician selecting the "maybe" button, then that point is maintained in the test list, and is, for example, put as the last point in the list, so that it is tested again before the test ends. Alternatively, the point may be placed at a random point in the remaining test point list, so that it does not necessarily appear last, but does appear subsequently. The point can then be tested again later in the test until a definitive answer is obtained from the clinician. In further examples it may be possible to keep a track of the number of times that a point has "maybe" recorded against it, such that it is only placed back into the test list a certain number of times such as, for example, once, twice, or three times at the maximum.

Regarding the ordering of test points in a test, preferably the display order of test points is such that the test subject is not able to discern a particular pattern or order to the test points, such that subject has some indication of where the next test point will be displayed based on those shown previously. Instead, a random or apparently random order of test points may be used.

If the clinician feedback is that the target graphic or video was not seen at the test point position, then again this result is logged at step 12.28. According to the settings of the test the test may then automatically add a point into the test, using an "auto add feature", to be described. If a test point is added in using the "auto add feature" then the new test point is added into the list, and although it may not be the next point to be tested, it will be tested before the test completes. When a point has been auto added into the test, processing then proceeds back to step 12.32, wherein it is determined whether there is a next point to test. Where a point has been auto added in to the test at step 12.30, there will always be a next point to test. Likewise, where a point has been kept in the list at step 12.38, similarly the test will continue.

Eventually, all of the test points will have been tested, and "yes" or "no" results stored against each point. Thereafter, the patient test results can be stored in the patient record, at step 12.34, and subsequently viewed by the clinician, as will be described later.

Turning first to FIG. 19, however, the operation of the "auto add" feature of step 12.30 will next be described.

FIG. 19 shows an example result plot of points that have been tested, to give a peripheral vision field plot, in this case for a subject's right eye. Result plot 190 comprises the positions of points that were tested 194, overlaid on a graticule 196. Each test point 194 is characterised by two values, firstly an angular value from either the vertical or horizontal lines of the plot, and secondly a magnitude value, also in degrees, indicating angle of gaze from the centre point out to the point. Thus, for example, a test point may have a position of 45°, being the rotational angle from the horizontal, or the vertical, and a magnitude of 50°, being the angle of view from the centre point, for a subject positioned in the centre.

The auto add function makes use of this definition of test points so as to add points into a test, the added points being of reduced magnitude, when a test point has not been spotted by a subject. Thus, for example, as shown in FIG. 19, an original test point was test point 1982, which has an angular rotational position of approximately 150° (assuming 0° is the positive X axis) and an angular magnitude of 50° (it is positioned on the 50° graticule line). In the event that this test point is not spotted by the test subject, and the auto add feature is enabled, an extra test point 1984 is added into the test template, having an identical rotational angular position, but a different angular magnitude. For example, in this case the angular magnitude has been reduced by 5°, so that the magnitude of point 1984 is 45°. This is then included in the test template, and a test graphic is in due course presented to the test subject at this position.

In this case, however, the test subject has still not spotted the test graphic at this position, and hence the auto add feature has added in a third test point 1986 of even small angular magnitude, but having the same rotational angular value. Thus, test point 1986 is of angular magnitude 40°. In this respect, it can be seen that the auto add feature has reduced the angular magnitude of each point by 5° each time. However, this step size can be set by the clinician user. In the case of FIG. 19, the second added test point 1986 has still not been spotted by the user when the test graphic is displayed thereat, and hence a third test point is added, being test point 1990. This has an even smaller angular magnitude of 35°. In this case, however, when the test graphic is presented to the user at this position, the user has seen the test graphic, such that it is not then necessary to add in further test points. However, in this example, the auto add feature has brought to light that the test subject has significant visual field loss in the lower left quadrant of his right eye, which should be investigated further.

Regarding the display order of points that have been added in to a test, as noted earlier an added point may not necessarily be the next test point to be displayed. Whilst in one embodiment an added test point at the same rotational angular position but smaller angular magnitude as a missed point may be displayed in order after the missed point i.e. it is the next point to be displayed after the missed point, in other embodiments an added point may be displayed later in the test series, after other points at different rotational angular positions have been displayed. By so doing, the test subject's attention is drawn away from the particular rotational angle region in which the missed test point(s) and any consequentially added test point(s) are located, and the test subject does not become alerted or suspicious to any unusually long gap in test images being displayed, such that their eyes may wander from the fixation image.

More particularly, imagine a test subject is viewing the fixation image at the fixation image position such as the center of the screen. If a point is then displayed that the test subject does not see, then a point will be added in at the same rotational angular position, but of lesser angular magnitude. However, depending on the time taken the test subject may by now have expected to see a test image, and may start to look around the test area, which would spoil the test. Therefore, in order to stop this, a test image at a different rotational angular position can be displayed, for example at a test position that the test subject has already been positively tested at i.e. at a location where the test subject saw the test image. Alternatively, another test point can be displayed to the subject, from the set of test points to be tested that have not yet been shown to the user. As such, the test subject is not alerted to the fact that a test point had to be added in, and the continuity of the test is maintained from the test subject view point.

In such a case, the point that has been added in is then displayed later in the test sequence, after one or more other test images at different rotational angles have been displayed to the test subject. If multiple points have to be added in at the same rotational angle, due to the reason that the test subject keeps missing the images (as in FIG. 19 and described above), then the same procedure as above may be used i.e. another test image at a different rotational angular position is displayed before the added-in test point is displayed at the problematic angular position where the user did not see the test image.

Figure 22:
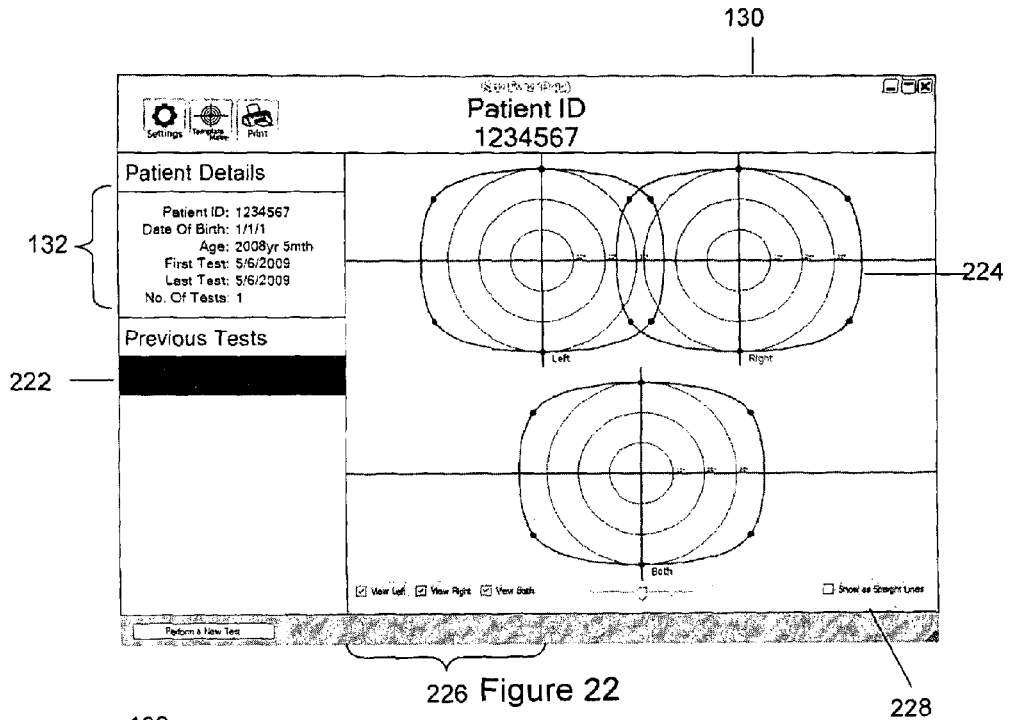
FIG. 22 is a further screen shot of the clinician screen in the second embodiment.

Turning now to how the test results may be reviewed, the clinician view module provides the ability to review a test that has just been performed, together with previous tests. In addition, the tests may be printed. FIG. 20 illustrates the steps involved in displaying test results. Firstly, at step 20.2 a patient ID is entered, and at step 20.4 the patient records are retrieved, and displayed. In this case, as shown in FIG. 22, if the patient has had a test performed then the results of that test will be stored with the patient record, and retrieved with the patient record for display to the clinician. FIG. 22 illustrates how the results of a test 222 are displayed to the clinician, as test plots 224, in the main clinician view. The test plots 224 can be displayed all at once, as shown, or may be displayed individually for each eye, or for binocular vision, by appropriate selection of check boxes 226. In addition, the plots may use bezier curves, as shown, to connect the points, or alternatively may, although perhaps less helpfully, connect the test points with straight lines, by the clinician ticking the "straight line" check box 228 in the GUI. In order to print the results, at step 20.10, the clinician may select the print icon in the top left of the GUI, and then the selected graphical records are printed.

Figure 23:
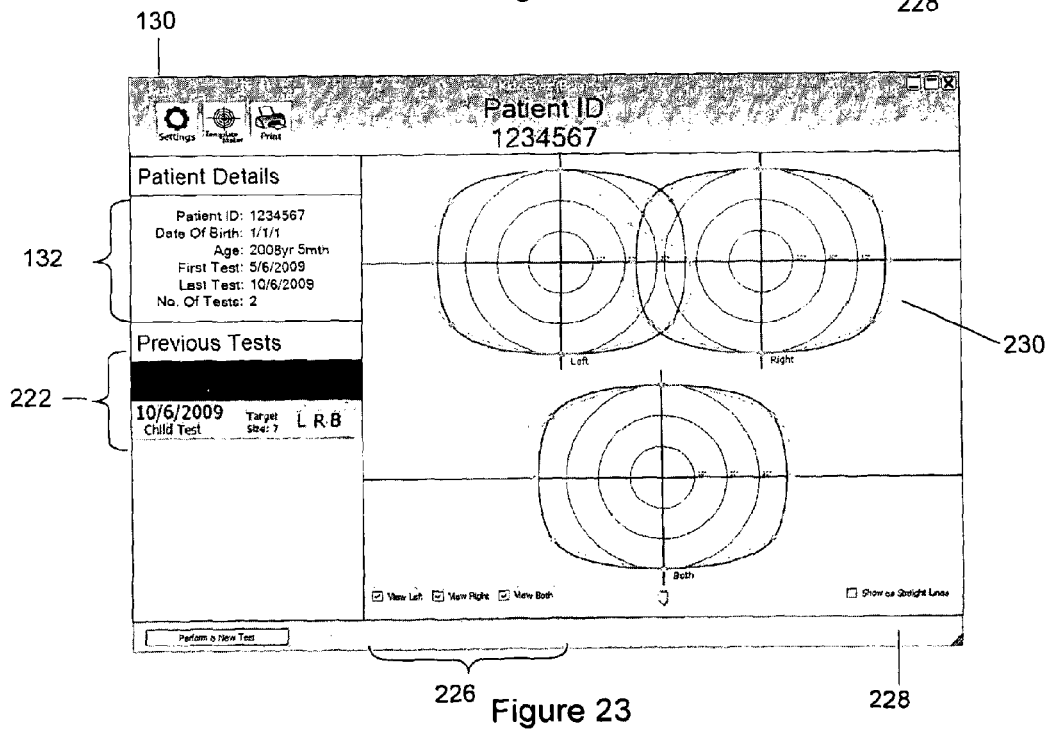
FIG. 23 is a further screen shot of the clinician screen in the second embodiment.

It is also possible to show multiple results, if multiple test results are available. The multiple results can be overlaid on top of each other for comparison, as shown in FIG. 23. In FIG. 23 it can be seen that two previous sets of test results are available in column 222, and that these are shown as overlaid test results 230. This view is useful for showing changes in peripheral vision fields. For example, in FIG. 23 it can be seen that the peripheral vision field of the subject's left eye has deteriorated markedly in the upper right quadrant. Multiple tests can be overlaid one on top of each other, and different colour plots are typically used to identify which test is which.

Figure 24:
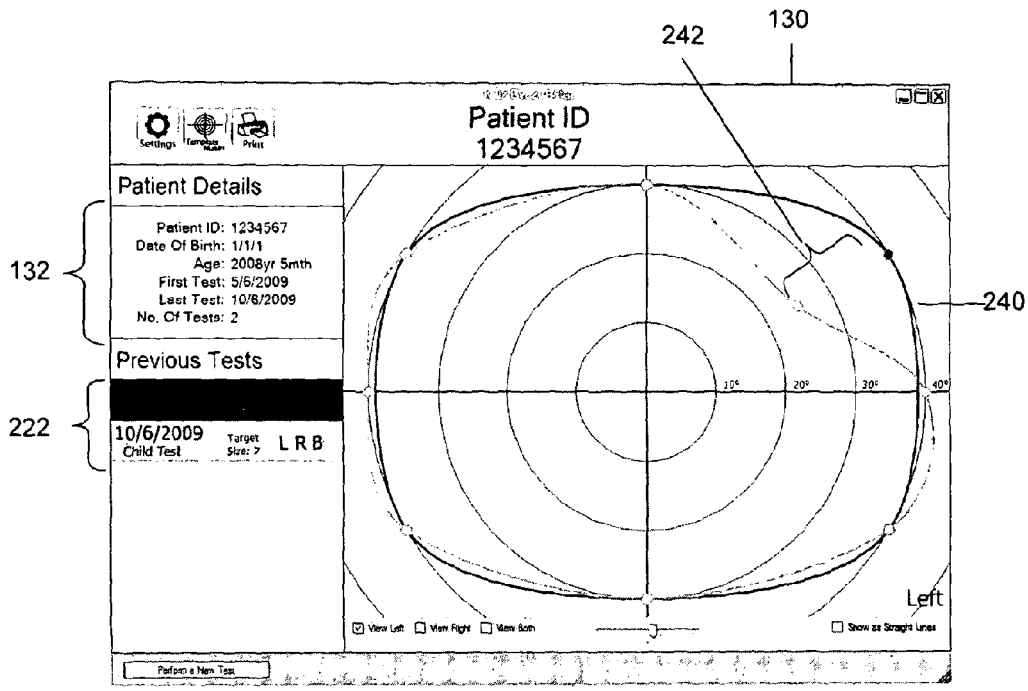
FIG. 24 is a further screen shot of the clinician screen in the second embodiment.

FIG. 24 illustrates how only a subset of multiple tests may be displayed. In particular, FIG. 24 illustrates multiple left eye plots, allowing the clinician to see in more detail the change in peripheral vision field in the upper right quadrant of the subject's left eye. In addition, here it can be seen that the auto add feature has been used to add in points on the second test as shown by the sequence of points 242 shown on the results.

In addition to the above described features, preferably the viewing feature also allows the clinician to zoom in to parts of the plot, and to scan and pan around the graphical result.

Figure 25:
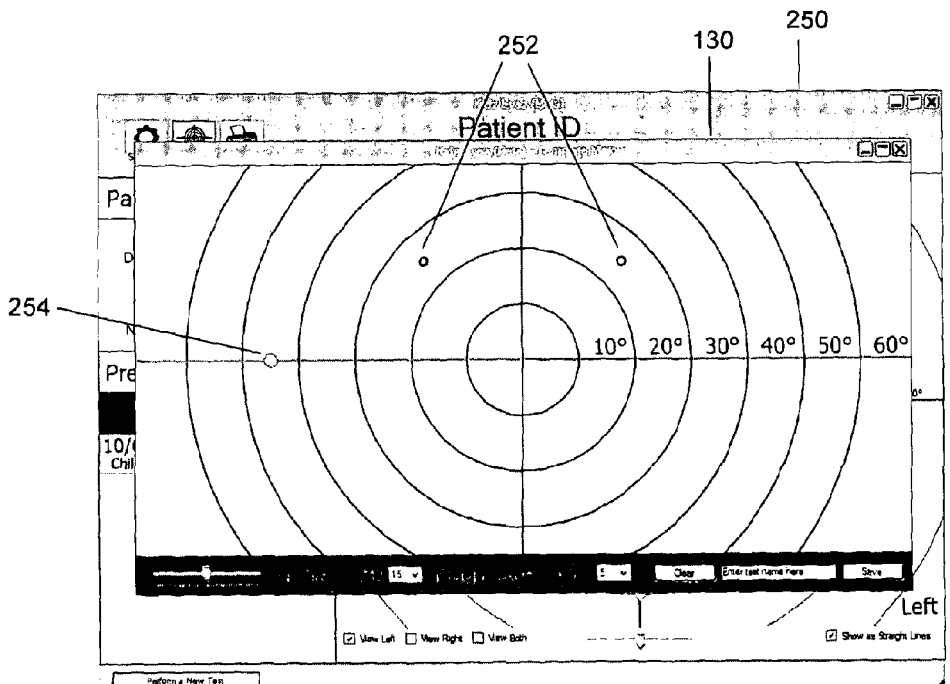
FIG. 25 is a further screen shot of the clinician screen illustrating a test template making tool used in the second embodiment.

As discussed previously, the measurement system also includes a template maker module, to allow a clinician to make new test templates, being sets of test points. This allows a clinician to design a test to try and focus on particular areas of a subject's peripheral vision. In order to produce a new test template then, as shown in FIG. 21, at step 21.2 the clinician selects a new template to be produced, using the "template maker" button in the GUI 130. This causes the new template maker graticule to be displayed at step 21.4, as shown in FIG. 25. The template maker graticule displays in a new window 250. Using a mouse pointer the clinician then marks on the template maker graticule the position of test points to be tested. As shown in FIG. 25, two points 252 have already been marked by the clinician, and the mouse cursor is shown as point 254. The template maker graticule can have a "snap" feature, to cause the cursor to snap to multiples of 1°, 5°, 10°, 15°, 20°, etc for both rotational angle and magnitude of the point. Alternatively, the clinician may place points wherever he or she wishes within the template maker graticule. To set a point the clinician simply moves the cursor 254 to the desired point, and clicks the mouse. The position is then stored as a new test point. Once the clinician has finished, and sufficient test points have been set, the set of points may be stored as a new test template, at step 21.8. That test template can then be selected for use at, for example, step 12.10 of the process of FIG. 12, described previously.

The provision of the template maker therefore allows a clinician to define tests to try and make a specific diagnosis or test particular areas of a subject's peripheral vision field in a simple and user friendly manner.

Overall, therefore, the peripheral vision measurement system of the second example provides a reliable and simple to use interface for performing peripheral vision tests, and allows for the easy management and display of test results. Testing of the system on live subjects has shown the reliability and feasibility of the system.

Various modifications may be made to the above described examples to provide further examples. For example, within the two examples described above a television type display screen such as a plasma, LCD, or LED display is used as the patient display. Alternatively, in other embodiments, a projection type display may be used. In this case, a video projector is used to display the fixation and target images onto a screen. A small hole may be cut in the screen at the centre, allowing the camera to be mounted behind the screen. This has advantages in that the camera is then not so prominent to the subject, and does not occlude any of the patient display screen. In addition, using a projection type system allows a larger image to be obtained than is the case with a display of fixed size such as a plasma, LCD, or LED screen. However, of course, where the size of the display changes due to projection characteristics, the positioning of the subject in terms of how far away from the display they are sat must be carefully made. The distance of the subject from the screen is a parameter that can be entered into the settings module of the application, to allow for automatic adjustment of target graphic and video positions.

In the above examples, it is described that the target graphic is preferably a video, of a theme selected by the clinician so as to be attractive to the child subject. One particularly preferable feature of using a video is that the same video can be used for both the fixation graphic, and the target graphic, without interruption. That is, the child subject starts watching a television program as part of the video content displayed at the fixation point, and then that video content is then continued in the target video at the target point position in a seamless manner. Thereafter the video is then continued at the fixation target when it is next displayed, followed by then being displayed at the next target point, and so on. Thus, as far as the child subject is concerned, all that happens through the test is that the position of the video on the screen changes, but that the story contained within the content is continued.

There are also several variations as to whether the fixation target is displayed at the same time as the target graphic or video. For example, it may be that the fixation target is a video, and is displayed constantly, with the target graphic then being either another video, or some other animated graphic to try and catch the child's attention away from the fixation video. However, it is thought that better results are obtained by removing the fixation video from the display screen when the target graphic is being shown. For some subjects, however, and particularly those who have performed the test before, removal of the fixation video may be an indicator that they should scan the rest of the screen to try and locate a target video. Therefore, to try and overcome this, for some tests it may be preferable to maintain the fixation target on the screen at the same time as the target graphic or video is being shown, so as to try and maintain the subject's attention on the fixation point, and thereby achieve better results.

In one example the fixation image may freeze at the last video frame displayed before the target image is displayed, and the freeze frame then continues to be displayed whilst the target image is displayed. The target image in such an example may be the video image (that then continues to play), or another image. Where another image is used the video soundtrack may continue to play, even though the video image to match the soundtrack is not being shown as either the fixation image, or the target image.

It will therefore be appreciated that there are several combinations of options as to format of the fixation images and the target images. The settings module provides settings to allow the clinician to chose any of the above options, depending on the subject.

Within the above first and second example the clinician display is augmented with indicators as to where the target graphic is presently been shown on the patient display, and also as to where the target graphic may next be shown. In the above example a colour coding system is used to distinguish whether the indicator shows that the target graphic is presently being displayed at the indicator location, or whether it is about to be displayed. In other examples instead of the colour of the indicator changing or otherwise being indicative, some other characteristic of the indicator is altered, for example its shape. For example, a square indicator may be used to show the position of where the target graphic is about to be displayed, and the shape of the indicator then changes to circular when the graphic is being displayed. In further examples two or more characteristics of the indicators may be altered, to try and convey more information. For example, both shape and colour may be used, with an indicator of a first shape illustrating a test point that has already been shown to the subject, and an indicator of a second shape illustrating test points that are about to be shown, or that are still to be shown in the future. The colour of the indicators of the first shape may indicate whether the point was seen by the user or nor. For example, a first colour may indicate that the point was seen, and a second colour may indicate that it was not. A third colour may be used to indicate that the point was a "maybe".

Within the above examples the images of the test subject are displayed to the clinician user throughout the test, and the clinician user makes a decision and provides feedback as to whether the subject saw a particular target point when it was displayed. In another example, however, instead of (or in addition to) the clinician reviewing the video images of the subject during the test the video images of the subject may be recorded for review by the clinician later. That is, whether displayed to the clinician in real time or not, the video images of the test subject performing the test may be stored, so that they may be reviewed by a clinician at a later time. In this respect, the video data is typically stored with the patient record.

Where the video images of the test subject are not to be shown to the clinician in real-time, then in another example the same display device (HDTV, computer monitor, etc.) may be used to display the video images to the clinician as was used to display the test images to the subject. Hence, some equipment re-use can be obtained.

In another example, where the video images of the test are recorded a clinician can then review the test video later and make decisions at that moment in time as to whether a child saw a target graphic or not. In this case as the video of the test is played back to the clinician user the clinician video display is preferably augmented with the indicators to show where the test graphic is about to be and then subsequently is being shown on the patient display, so that the clinician has the same experience as if he or she was conducting the test live. Therefore, as well as storing the video image data test meta data synchronised with the video data is also stored that instructs the clinician view module to augment the clinician video display with target point position indicators even when the video being shown is recorded video.

The above example allows a clinician to review a test at a later time, and hence allows tests to be performed even when a clinician is not available at the time the test is to be performed. However, because the clinician is not available to make a decision as to whether a target point was seen during the test, then the "auto-add" feature previously described becomes less useful. Instead, tests can be designed with test points which display target graphics or videos across the whole field of the view of the test subject, rather than trying to restrict test points to the edge of the vision field, and then adaptively adding test points in.

In other examples it will also be understood that, whether based on recorded test imagery or live test imagery, the clinician need not be co-located with the test subject, and that the clinician may be located at a separate display located in another room, building, city, country, or even continent, with the video imagery of the test subject then being provided to the clinician's computer over a network. In this case typically two control computers are required, being one to operate the patient display, and one to operate the clinician display. One of the computers may operate in a server mode, and perform most of the processing, controlling the client terminal to produce the appropriate display. For example, the computer at the clinician end may contain most of the software, and store test results, patient records, and the like, and control the patient display remotely by virtue of a relatively dumb client installed on a computer co-located with the patient display.

In another example, the application may be completely network based, and run on a network server which is not located with either the patient display or clinician display. In this case, the patient display and clinician displays can run relatively lightweight dumb clients, with most of the processing then performed over a network by the network server. Patient records, test results, test video, and the like can be stored at the network server, or alternatively elsewhere on another storage server to which the network server running the testing system has access.

In the above first and second example the clinician is relied upon to review the video imagery of the test subject and decide if the subject's direction of gaze moves towards a test point when the target graphic or video is displayed on the patient screen at that location. However, in a further example this decision making process of the clinician may be replaced by an image processing function, such as, for example, the template matching techniques described by Suga et al, supra. In such an example the video images of the test subject are processed by the template matching image processing algorithm to determine if the subject's direction of gaze moves towards a target graphic or video when displayed, and the results then recorded automatically. In this example, there is no need to provide the clinician display, although such a display may be provided for monitoring purposes. In addition, if the image processing algorithm determines that a target is not seen then the auto-add function described above can be used to add in an easier test point, which can then be presented to the test subject. In this respect, the image processing algorithm replaces the receipt of the clinician feedback of step 12.20 of FIG. 12, but in all other respect the processing and operation can remain identical. For example, continuous video may be used for the target and fixation points.

The auto add function is particularly advantageous, and can be used where the decision as to whether a target was seen by the subject at a test point is made either by the clinician user, or using image processing techniques. In particular the auto add function allows the location of the test points to be adapted dynamically during the test, such that the most accurate plot of a subject's visual field can be obtained as possible. In particular, by incrementally adjusting the angular magnitudes of the test points, so as to reduce the angular magnitude, the extent of a subject's visual field can be adaptively explored during a test, so as to determine the visual field extent.

In another example, where an automatic gaze tracking technique is used, such as in Suga et al, in order to supplement the image processing algorithm that is used to track the eye position the head position can also be independently tracked using natural or other face-attached features to resolve head position. For example, a fiducial, calibration sticker may be placed on the eye patch (which is already worn by the subject when one eye at a time is being tested). One problem in automated eye tracking techniques is to resolve the subject head position in the first place, from which the eye position and direction of gaze can then be determined. In other words, eye-in-space=eye-in-head+head-in-space. By using a known calibration symbol such as a cross or some other easy-to-recognise symbol displayed to the camera on the outer surface of the eye patch, head position can be readily resolved in an image by looking for the known symbol shape. Once head position has been established in the image, then identification of eye position within the image becomes more straightforward. That is, spatial segmentation of the images to be processed becomes easier, as there is a generally known a priori relationship between the position of the calibration symbol, and the head orientation and position of the test subject.

In a further example where image processing to provide automatic gaze tracking in used, as well as providing spatial segmentation of an image using a known calibration symbol as described above, in addition or alternatively it is also possible to temporally segment a video stream, to reduce the number of video images that need to be processed. More particularly, because the system knows precisely when target images will be displayed to the test subject (since the system generates and controls display of the target images), then it only becomes necessary to image process the few video frames before and after the target image event (probably at most 1.0 sec=0.5 sec+0.5 sec of footage each side) to determine eye gaze direction of the subject. At other times the direction of gaze of the subject is generally irrelevant.

One caveat to the above is that the subject should preferably be viewing the fixation image at the time the target image is to be displayed. Only if this is the case is an accurate test of peripheral vision performed, as if the subject is looking elsewhere on the screen when a target image is shown the relative position of the target image in the subject's field of view will be different than the case where the subject if looking at the fixation image. Therefore, in another example eye gaze determination is performed in advance of a target image being shown, to determine whether the subject is looking at the fixation image, or at another part of the screen. Display of the target image is then adapted in dependence on the determination as to whether the subject is looking at the fixation image, in that the display may be delayed until the subject's gaze returns to the fixation image. In this way target images are shown when the subject is looking at the fixation image, and hence test accuracy can be improved.

Within the above example the determination as to whether the test subject is looking at the fixation image may be performed automatically, for example by an image processing algorithm such as Suga et al, or by the clinician. In the latter case, the clinician GUI may further comprise a button which is activated by the clinician during the test to indicate to the system that the test subject is looking at the fixation image before a target image is to be displayed. Once the clinician activates the button the system then proceeds to display the target image at the indicated target location.

In another example of the invention an automated eye tracking algorithm such as Suga et al can be combined in hybrid use with the augmented clinician view in a semi-automated fashion. For instance, an automated analysis of the 1 sec eye movement clips per target mentioned above can be done to enhance accuracy by catching false positives and negatives, either as: a) automatically for each target after it appears (e.g. giving percentage confidence) during the course of a manual, augmented-view test run by the clinician; b) in batch for the full test sequence at the end of the augmented-view test run by the clinician; or c) automatically (as in Suga), instead of an augmented-view clinician test but followed with full or partial manual augmented-view human-based testing by the clinician. The latter human confirmation will be very rapid as it will merely run through the 1 sec (or shorter) clips, or even organise them usefully in a combined full-screen view pointing to the targets of most interest to review for accuracy. Such a human review could also be done during the course of the test, if the system is allowed to function automatically for some of the time during the process.

Thus, even where an automated gaze-tracking system is used to perform peripheral vision tests, such as in Suga et al, such an automated system can be complemented by the augmented clinician view of the previous examples described above, to allow the clinician to check the results of the automated system, and to increase confidence levels in each result. Alternatively, where, as in the first and second main examples described above, the clinician is the primary determiner of whether a target image was seen, an automated image processing system may be used as back up to check the clinician determined results, and increase the confidence in each test result. As noted, this image processing may be performed as a test progresses, or in batch at the end of the test, preferably by processing the time segmented video stream, so as to process only those video frames around the time the target images were displayed.

Various further modifications, whether by way of addition, deletion, or substitution will be apparent to the intended reader, being a person skilled in the art, to provide further examples, any and all of which are intended to fall within the appended claims.

The invention claimed is:

1. A peripheral vision measurement system, comprising:
a subject video display arranged to display test images to a test subject;
a camera arranged to capture images of the test subject;
a user video display arranged to display captured images of the test subject to a user; and
one or more processors arranged to control the subject and user video displays, the user display being controlled so as to be augmented with at least one indicator relating to the position of a test image on the subject display, wherein the one or more processors are further arranged to use determination data as to whether the test subject has seen a test image when displayed on the subject video display, said determination data being recorded against the position of the test image when displayed on the subject video display, whereby to collate measurement data indicative of the peripheral vision field of the test subject, wherein the one or more processors have at least one input arranged to receive feedback data from the user relating to the displays, the feedback data relating to a judgment by the user as to whether the test subject has seen a test image when displayed on the subject video display, the feedback data being used as said determination data.

2. A peripheral vision measurement system, comprising:
a subject video display arranged to display test images to a test subject;
a camera arranged to capture images of the test subject;
a user video display arranged to display captured images of the test subject to a user; and
one or more processors arranged to control the subject and user video displays, the user display being controlled so as to be augmented with at least one indicator relating to the position of a test image on the subject display, wherein the one or more processors are further arranged to use determination data as to whether the test subject has seen a test image when displayed on the subject video display, said determination data being recorded against the position of the test image when displayed on the subject video display, whereby to collate measurement data indicative of the peripheral vision field of the test subject, wherein multiple test images are shown to the test subject at different positions on the subject display and multiple determination data received relating to the multiple positions stored such that a set of peripheral vision test results is created, the system further comprising one or more storage media arranged to store the set(s) of test results, and from which the set(s) of test results can be retrieved for later viewing, wherein multiple sets of test results may be stored for the same test subject, and subsequently viewed simultaneously.

3. A peripheral vision measurement system, comprising:
a subject video display arranged to display test images to a test subject;
a camera arranged to capture images of the test subject;
a user video display arranged to display captured images of the test subject to a user; and
one or more processors arranged to control the subject and user video displays, the user display being controlled so as to be augmented with at least one indicator relating to the position of a test image on the subject display, wherein the one or more processors are further arranged to use determination data as to whether the test subject has seen a test image when displayed on the subject video display, said determination data being recorded against the position of the test image when displayed on the subject video display, whereby to collate measurement data indicative of the peripheral vision field of the test subject, wherein multiple test images are shown to the test subject at different positions on the subject display and multiple determination data received relating to the multiple positions stored such that a set of peripheral vision test results is created, the system further comprising one or more storage media arranged to store the set(s) of test results, and from which the set(s) of test results can be retrieved for later viewing, wherein a set of test results is plotted graphically to allow for graphical viewing by the user, multiple sets of test results being overlaid on the same graphical plot.

* * * * *